US006955810B2

(12) United States Patent
Gotwals et al.

(10) Patent No.: US 6,955,810 B2
(45) Date of Patent: Oct. 18, 2005

(54) METHOD FOR THE TREATMENT OF INFLAMMATORY DISORDERS

(75) Inventors: Philip Gotwals, Needham, MA (US); Antonin DeFougerolles, Brookline, MA (US); Roy Lobb, Westwood, MA (US); Victor Kotelianski, Boston, MA (US)

(73) Assignee: Biogen Idec, Inc., Cambridge, MA (US)

( * ) Notice: Subject to any disclaimer, the term of this patent is extended or adjusted under 35 U.S.C. 154(b) by 0 days.

(21) Appl. No.: 09/996,738

(22) Filed: Nov. 30, 2001

(65) Prior Publication Data

US 2002/0146417 A1 Oct. 10, 2002

Related U.S. Application Data

(63) Continuation of application No. PCT/US00/15004, filed on Jun. 1, 2000.
(60) Provisional application No. 60/185,336, filed on Feb. 29, 2000, and provisional application No. 60/137,038, filed on Jun. 1, 1999.

(51) Int. Cl.[7] ....................... A61K 39/395; C07K 16/28
(52) U.S. Cl. ............................... 424/144.1; 424/152.1; 530/388.22
(58) Field of Search ........................... 424/124.1, 139.1, 424/173.1, 175.1, 152.1; 530/386.22, 355.7

(56) References Cited

U.S. PATENT DOCUMENTS 5,788,966 A  8/1998 Chess et al.

FOREIGN PATENT DOCUMENTS

JP  08-131185  5/1996

OTHER PUBLICATIONS

Rikonen et al. Antibody against human alpha 1 beta 1 integrin inhibits HeLa cell adhesion to laminin and to type I, IV, and V collagens. Biochem Biophys Res Commun.;209(1):205–212, 1995.*
Briesewitz etal., 1993, Journal of Biological Chemistry, 268:2989–2996, "Expression of Native and Truncated Forms of the Human Integrin al Subunit".
Fabbri et al, 1996, Tissue Antigens, 48:47–51, "A functional monoclonal antibody recognizzing the human alpha1–integrin I–domain".
Gotwals, et al. 1999, biochemistry 38:8280–8288, "Divalent Cations Stabilize the alb1 Integrin I Domain".
Kern et al., 1994, Journal of Biological Chemistry, 269:22811–22816, "The Role of the I Domain in Ligand Binding of the Human Integrin a1b1".
Laffon et al. 1989 Arthritis and Rheumatism 32:386–392, "Very Late Activation Antigen of Synovial Fluid T cells from Patients with Rheumatoid Arthritis and other Rheumatic Diseases".

* cited by examiner

Primary Examiner—Christina Chan
Assistant Examiner—Maher Haddad
(74) Attorney, Agent, or Firm—Kevin J. McGough; Coleman Sudol Sapone, PC

(57) ABSTRACT

A method for the treatment of inflammatory disorders is disclosed, particularly the treatment of arthritis. The method comprises the administration of a function blocking antibody which is capable of binding an epitope of VLA-1.

7 Claims, 19 Drawing Sheets

METHOD FOR THE TREATMENT OF INFLAMMATORY DISORDERS

RELATED APPLICATIONS

This is a continuation of PCT/US00/15004, filed on Jun. 1, 2000, which claims priority from U.S. provisional application Ser. No. 60/185,336 filed on Feb. 29, 2000 and U.S. provisional application Ser. No. 60/137,038 filed on Jun. 01, 1999.

BACKGROUND OF THE INVENTION

Integrins are cell surface protein complexes that form a large class of cell-surface molecules mediating adhesion of cells to each other and their surrounding. Cells need to adhere to each other and to other molecules in their environment in many developmental and physiological processes. Examples include the creation of tissues and organs and the maintenance of their integrity. Including amongst these physiological processes are inflammatory disorders.

One of the key steps during the inflammatory process involves the extravasation of cells out of the blood vessels, into the tissues, and towards the site of infection. The role of adhesion molecules in this process is often broken down into a three step model involving initial leukocyte 'rolling' on inflamed endothelium, followed by firm attachment, and resulting in transendothelial migration of leukocytes into the inflamed tissues (Hynes, R. O. 1992 *Cell* 69:11–25; Springer, T. A. 1992 *Cell* 76:301–314). A further critical step in the inflammatory cascade, and one that has not been extensively explored, occurs within the peripheral tissues where infiltrating, as well as resident cells, need to migrate towards the site of infection, recognize foreign antigen, and undergo cellular activation in order to perform their effector functions. To directly assess the importance in inflammation of interstitial adhesive interactions in isolation from the role adhesive interactions play in leukocyte recruitment, we have focused on the importance of adhesion molecules of the integrin family and fragments thereof, and their role in animal models of inflammation, particularly arthritis.

SUMMARY OF THE INVENTION

The present invention provides a method for treatment of inflammatory disorders in a subject. Specifically, the invention provides a method for treatment of arthritis.

More particularly, the invention provides a method for the treatment of an inflammatory disorder in a subject comprising administering to the subject a pharmaceutical composition comprising an effective amount of an α1β1 function blocking antibody or a fragment of the antibody, wherein the α1β1 function blocking antibody or fragment is capable of binding an epitope of VLA-1 comprising amino acid residues 91–96, Val-Gln-Arg-Gly-Gly-Arg.

The anti-integrin antibody can be selected from the group consisting of a human antibody, a chimeric antibody, a humanized antibody and fragments thereof. The anti-integrin antibody can be a monoclonal or polyclonal antibody.

The invention further provides a method for treating inflammatory disorders in a subject that is a human or animal subject.

All of the cited literature in the preceding section, as well as the cited literature included in the following disclosure, are hereby incorporated by reference.

DESCRIPTION OF THE DRAWINGS

FIG. 15. FIG. 15 illustrates the amino acid sequence of the human α1-I integrin polypeptide sequence. The amino acid sequence of the epitope for the anti-α1-I domain blocking mAbs (SEQ ID NO:8) is shown in the box.

DETAILED DESCRIPTION OF THE INVENTION

Figure 1A:
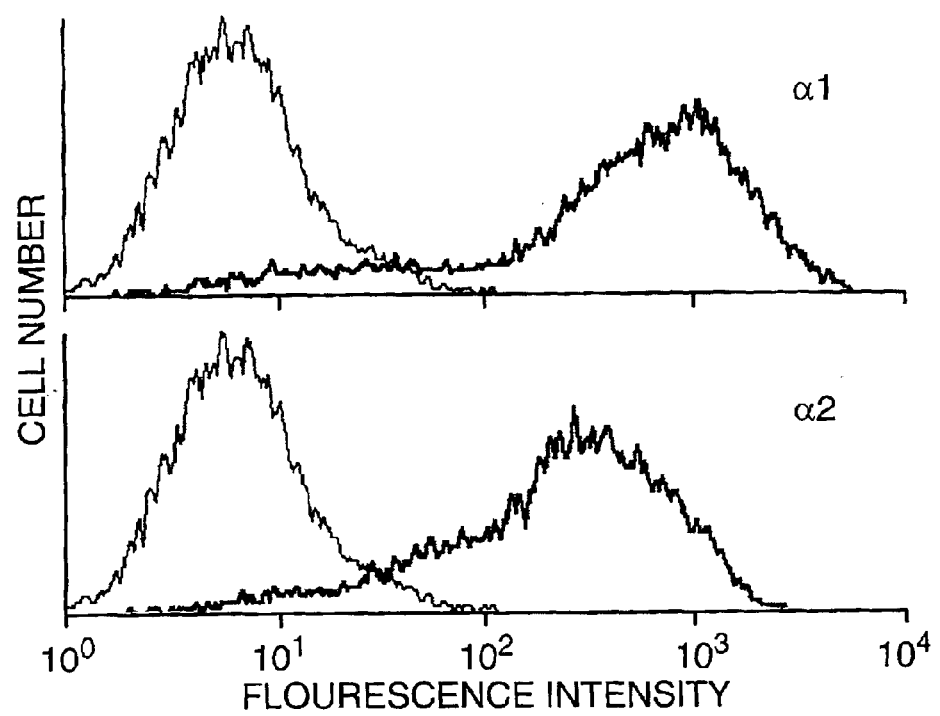
FIG. 1. Collagen-binding integrins α1β1 and α2β1 on activated leukocytes. (A). Flow cytometric analysis of α1 and α2β1 integrin expression on IL-2-activated splenocytes (d 11). Cells were labeled with either anti-α1 mAb, anti-α2 mAb, or non-binding control mAb (grey lines), and followed by FITC-anti-hamster immunoglobulin. (B) Effect of anti-α1 and anti-α2 mAbs on leukocyte adhesion to collagen. $10^5$ IL-2 activated splenocytes were treated with indicated mAbs for 15 min before plating onto either type IV or type I collagen-coated wells for 1 h at 37° C. Adhesion was calculated as illustrated in Example 1, and expressed as % adhesion relative to control mAb-treated cells. Adhesion assays were done in triplicate, and at least three independent experiments were performed. One representative experiment is shown.

It is a discovery of the present invention that an antibody to an integrin and fragment thereof, particularly, an α1-integrin subunit, can block the interaction of pro-inflammatory leukocytes with components of the extracellular matrix including, but not limited to collagens, laminin and fibronectin. While not intending to limit the invention to any single mechanism of action it is proposed that disruption of the interaction between the integrin and fragment thereof and the surrounding matrix may decrease the expression of pro-inflammatory cytokines. It is further proposed that antibodies to integrins and fragments thereof may be modulating the effector phases of inflammatory responses by acting at the level of the antigen-specific T cell. In addition, it is proposed that antibodies to integrins and fragments thereof may act by disrupting cell migration within tissues and/or effects on cellular priming and activation within tissues.

This discovery illustrates the importance of adhesion molecules of the integrin family, particularly α1β1, in the peripheral tissue environment during conditions related to inflammation. It also extends the role of integrins family and fragments thereof in inflammation beyond leukocyte attachment and extravasation at the endothelial interface by highlighting the importance of the matrix-rich peripheral tissue environment to immune responses and it reveals peripheral tissues as a new point of intervention for adhesion based therapies.

The methods of the present invention contemplate the use of antibodies to integrins where the integrins contemplated include molecules which comprise a β chain, including but not limited to β1, β2, β3, β4, β5, β6, β7, β8, non-covalently bound to an α chain, including but not limited to α1, α2, α3, α4, α5, α6, α7, α8, α9, α10, αV, αL, αM, αX, αD, αE, αIIb. Examples of the various integrins contemplated for use in the invention include, but are not limited to:

α1β1, α2β1, α3β1, α4β1, α5β1, α6β1, α7β1, α8β1, α9β1, α10β1, αVβ1, αLβ1, αMβ1, αXβ1, αDβ1, αIIbβ1, αEβ1;

α1β2, α2β2, α3β2, α4β2, α5β2, α6β2, α7β2, α8β2, α9β2, α10β2, αVβ2, αLβ2, αMβ2, αXβ2, αDβ2, αIIbβ2, αEβ2;

α1β3, α2β3, α3β3, α4β3, α5β3, α6β3, α7β3, α8β3, α9β3, α10β3, αVβ3, αLβ3, αMβ3, αXβ3, αDβ3, αIIbβ3, αEβ3;

α1β4, α2β4, α3β4, α4β4, α5β4, α6β4, α7β4, α8β4, α9β4, α10β4, αVβ4, αLβ4, αMβ4, αXβ4, αDβ4, αIIbβ4, αEβ4;

α1β5, α2β5, α3β5, α4β5, α5β5, α6β5, α7β5, α8β5, α9β5, α10β5, αVβ5, αLβ5, αMβ5, αXβ5, αDβ5, αIIbβ5, αEβ5;

α1β6, α2β6, α3β6, α4β6, α5β6, α6β6, α7β6, α8β6, α9β6, α10β6, αVβ6, αLβ6, αMβ6, αXβ6, αDβ6, αIIbβ6, αEβ6;

α1β7, α2β7, α3β7, α4β7, α5β7, α6β7, α7β7, α8β7, α9β7, α10β7, αVβ7, αLβ7, αMβ7, αXβ7, αDβ7, αIIbβ7, αEβ7;

α1β8, α2β8, α3β8, α4β8, α5β8, α6β8, α7β8, α8β8, α9β8, α10β8, αVβ8, αLβ8, αMβ8, αXβ8, αDβ8, αIIbβ8, αEβ8;

The methods of the present invention also contemplate the use of antibodies to integrin fragments including for example antibodies to a β chain alone, including but not limited to β1, β2, β3, β4, β5, β6, β7, β8, as well as an α chain alone, including but not limited to α1, α2, α3, α4, α5, α6, α7, α8, α9, α10, αV, αL, αM, αX, αD, αE, αIIb. In addition, the methods of the present invention further contemplate the use of antibodies to integrin fragments including for example antibodies to the I domain of the α chain, including but not limited to the I domain from α1β1 (Briesewitz et al., 1993 J. Biol. Chem. 268:2989); α2β1 (Takada and Hemler, 1989 J Cell Biol 109:397), αLβ2 (Larson et al., 1989 J Cell Biol 108:703), αMβ2 (Corbi et al., 1988 J Biol Chem 263:12403), αXβ2 (Corbi et al., 1987 EMBO J 6:4023), αDβ2 (Grayson et al., 1988 J Exp Med 188:2187), αEβ7 (Shaw et al., 1994 J Biol Chem 269:6016). In a preferred embodiment, the α1-I domain antigenic determinant comprises an amino acid sequence of at least 6 contiguous amino acids, wherein the contiguous sequence is found within the sequence of FIG. 15. Moreover, in a preferred embodiment, the contiguous sequence is Val-Gln-Arg-Gly-Gly-Arg.

Methods for producing integrins for use in the present invention are known to those of skill in the art (see for e.g. Springer et al. 1990, *Nature* 346:425–434).

Embodiments of the present invention further include anti-integrin polyclonal and monoclonal antibodies. Preferred embodiments of the present invention include a monoclonal antibody such an anti-α1 monoclonal antibody.

Figure 15:
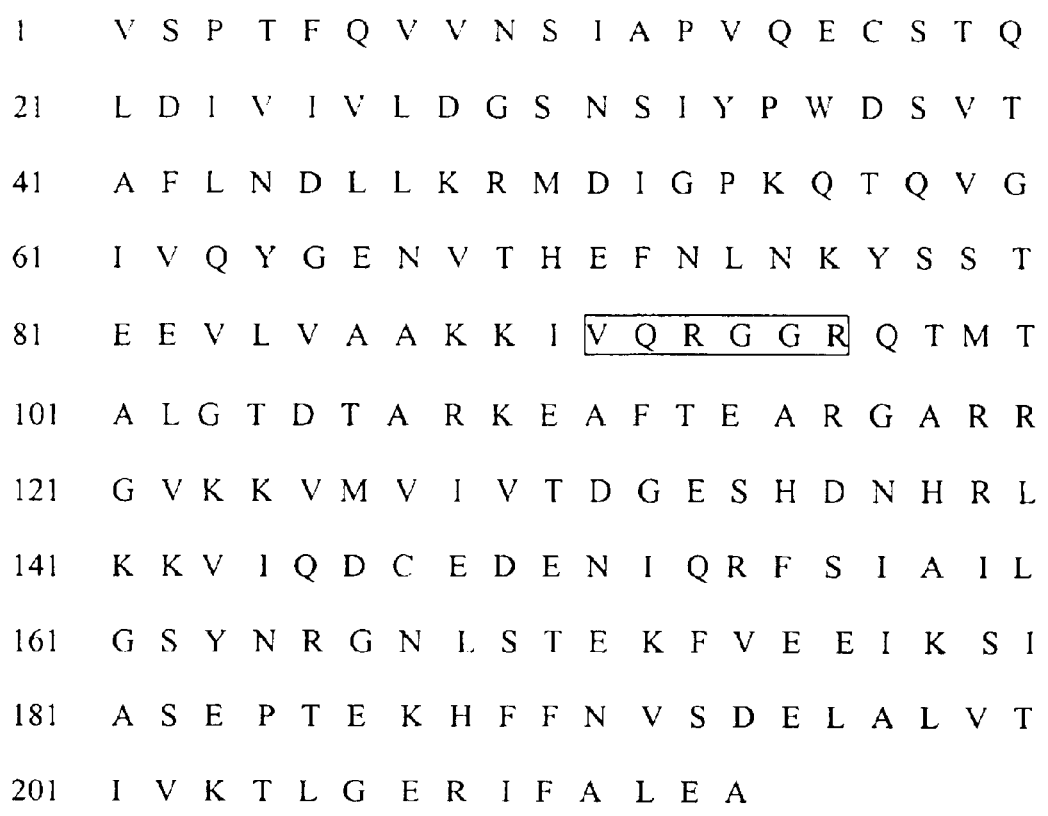

An α1β1 function blocking antibody as used herein refers to an antibody that binds to the α1-I domain, specifically at an epitope identified by amino acids 91–96 of FIG. 15, and that blocks α1β1 function as tested for, by example, the ability to inhibit K562-α1 dependent adhesion to Collagen IV (see Example 15).

Preferred antibodies and homologs for treatment, in particular for human treatment, include human antibody homologs, humanized antibody homologs, chimeric antibody homologs, Fab, Fab', F(ab')2 and F(v) antibody fragments, and monomers or dimers of antibody heavy or light chains or mixtures thereof. Thus, monoclonal antibodies against an integrin molecule and fragment thereof are the preferred binding agent in the method of the invention.

As used herein, the term "antibody homolog" includes intact antibodies consisting of immunoglobulin light and heavy chains linked via disulfide bonds. The term "antibody homolog" is also intended to encompass a protein comprising one or more polypeptides selected from immunoglobulin light chains, immunoglobulin heavy chains and antigen-binding fragments thereof which are capable of binding to one or more antigens (i.e., α1, α2, α6 or alpha-I domain containing integrin subunits). The component polypeptides of an antibody homolog composed of more than one polypeptide may optionally be disulfide-bound or otherwise covalently crosslinked.

Accordingly, therefore, "antibody homologs" include intact immunoglobulins of types IgA, IgG, IgE, IgD, IgM (as well as subtypes thereof), wherein the light chains of the immunoglobulin may be of types kappa or lambda.

"Antibody homologs" also include portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like. Thus, antigen-binding fragments, as well as full-length dimeric or trimeric polypeptides derived from the above-described antibodies are themselves useful.

As used herein, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain.

As used herein, a "chimeric antibody homolog" is an antibody homolog, produced by recombinant DNA technology, in which all or part of the hinge and constant regions of an immunoglobulin light chain, heavy chain, or both, have been substituted for the corresponding regions from another immunoglobulin light chain or heavy chain. In another aspect the invention features a variant of a chimeric molecule which includes: (1) an integrin targeting moiety; (2) optionally, a second peptide, e.g., one which increases solubility or in vivo life time of the integrin targeting moiety, e.g., a member of the immunoglobulin super family or fragment or portion thereof, e.g., a portion or a fragment of IgG, e.g., the human IgG1 heavy chain constant region, e.g., CH2 and CH3 hinge regions; and a toxin moiety. The chimeric molecule can be used to treat a subject, e.g., a human, at risk for disorder related to proliferation of epithelial cells such as hair follicles and the like.

As used herein, a "human antibody homolog" is an antibody homolog produced by recombinant DNA technology, in which all of the amino acids of an immunoglobulin light or heavy chain that are derived from a human source.

As used herein, "an inflammatory disorder", includes, but is not limited to, such disorders as, skin related conditions such as psoriasis, eczema, burns and dermatitis. Other inflammatory disorders contemplated for treatment by the methods of the present invention include but are not limited to the treatment of asthma, bronchitis, menstrual cramps, tendinitis, bursitis, and the treatment of pain and headaches, or as an antipyretic for the treatment of fever. The methods of the invention also would be useful to treat gastrointestinal conditions such as inflammatory bowel disease, Crohn's disease, gastritis, irritable bowel syndrome and ulcerative colitis and for the prevention of colorectal cancer. The methods of the invention would be useful in treating inflammatory disorders in such diseases as vascular diseases, migraine headaches, periarteritis nodosa, thyroiditis, aplastic anemia, Hodgkin's disease, rheumatic fever, type I diabetes, myasthenia gravis, multiple sclerosis, sarcoidosis, nephrotic syndrome, Behcet's syndrome, polymyositis, gingivitis, hypersensitivity, conjunctivitis, swelling occurring after injury, myocardial ischemia, and the like. The methods of the invention are also useful in the treatment of allergic rhinitis, respiratory distress syndrome, endotoxin shock syndrome, and atherosclerosis.

In a preferred embodiment, the methods of the invention are useful in the treatment of arthritis, including for example, rheumatoid arthritis and osteoarthritis.

An "effective amount" is an amount sufficient to effect beneficial or desired clinical results. An effective amount can be administered in one or more administrations. In terms of treatment of an inflammatory disorder, an "effective amount" of an anti-integrin antibody is an amount sufficient to palliate, ameliorate, stabilize, reverse, slow or delay progression of an inflammation-related condition in accordance with clinically acceptable standards for disorders to be treated or for cosmetic purposes. Detection and measurement of indicators of efficacy may be measured by a number of available diagnostic tools, including but not limited to, for example, by physical examination including blood tests, pulmonary function tests, and chest X-rays; CT scan; bronchoscopy; bronchoalveolar lavage; lung biopsy and CT scan.

The technology for producing monoclonal antibodies, including for example, anti-integrin monoclonal antibodies is well known. See for example, Mendrick et al. 1995, $Lab.$ $Invest.$ 72:367–375 (mAbs to murine anti-$\alpha1\beta1$ and anti-$\alpha2\beta1$); Sonnenberg et al. 1987 $J.$ $Biol.$ $Chem.$ 262:10376–10383 (mAbs to murine anti-$\alpha6\beta1$); Yao et al. 1996, $J$ $Cell$ $Sci$ 1996 109:3139–50 (mAbs to murine anti-$\alpha7\beta1$); Hemler et al. 1984, $J$ $Immunol$ 132:3011–8 (mAbs to human $\alpha1\beta1$); Pischel et al. 1987 $J$ $Immunol$ 138:226–33 (mAbs to human $\alpha2\beta1$); Wayner et al. 1988, $J$ $Cell$ $Biol$ 107:1881–91 (mAbs to human $\alpha3\beta1$); Hemler et al. 1987 $J$ $Biol$ $Chem$ 262:11478–85 (mAbs to human $\alpha4\beta1$); Wayner et al. 1988 $J$ $Cell$ $Biol$ 107:1881–91 (mAbs to human $\alpha5\beta1$); Sonnenberg et al. 1987, $J.$ $Biol.$ $Chem.$ 262:10376–10383 (mAbs to human $\alpha6\beta1$); A Wang et al. 1996 $Am.$ $J.$ $Respir.$ $Cell$ $Mol.$ $Biol.$ 15:664–672 (mAbs to human $\alpha9\beta1$); Davies et al. 1989 $J$ $Cell$ $Biol$ 109:1817–26 (mAbs to human $\alpha$V $\beta1$); Sanchez-Madrid et al. 1982, $Proc$ $Natl$ $Acad$ $Sci$ $USA$ 79:7489–93 (mAbs to human $\alpha$L $\beta1$); Diamond et al. 1993, $J$ $Cell$ $Biol$ 120:1031–43 (mAbs to human $\alpha$M$\beta2$); Stacker et al. 1991 $J$ $Immunol$ 146:648–55 (mAbs to human $\alpha$X$\beta2$); Van der Vieren et al 1995 $Immunity$ 3:683–90 (mAbs to human $\alpha$D$\beta2$); Bennett et al. 1983 $Proc$ $Natl$ $Acad$ $Sci$ $USA$ 80:2417–21 (mAbs to human $\alpha$IIb$\beta3$); Hessle et al. 1984, $Differentiation$ 26:49–54 (mAbs to human $\alpha6\beta4$); Weinacker et al. 1994 $J$ $Biol$ $Chem$ 269:6940–8 (mAbs to human $\alpha$V$\beta5$); Weinacker et al. 1994 $J$ $Biol$ $Chem$ 269:6940–8 (mAbs to human $\alpha$V$\beta6$); Cerf-Bensussan et al 1992 $Eur$ $J$ $Immunol$ 22:273–7 (mAbs to human $\alpha$E$\beta7$); Nishimura et al. 1994 $J$ $Biol$ $Chem$ 269:28708–15 (mAbs to human $\alpha$V$\beta8$); Bossy et al. 1991 $EMBO$ $J$ 10:2375–85 (polyclonal antisera to human $\alpha8\beta1$); Camper et al. 1998 $J.$ $Biol.$ $Chem.$ 273:20383–20389 (polyclonal antisera to human $\alpha10\beta1$).

In general, an immortal cell line (typically myeloma cells) is fused to lymphocytes (typically splenocytes) from a mammal immunized with whole cells expressing a given antigen, e.g., an integrin, and the culture supernatants of the resulting hybridoma cells are screened for antibodies against the antigen. See, generally, Kohler et at., 1975, Nature 265: 295–497, "Continuous Cultures of Fused Cells Secreting Antibody of Predefined Specificity".

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-integrin antibodies may be identified by immunoprecipitation of 125I-labeled cell lysates from integrin-expressing cells. Antibodies, including for example, anti-integrin antibodies, may also be identified by flow cytometry, e.g., by measuring fluorescent staining of antibody-expressing cells incubated with an antibody believed to recognize integrin molecules. The lymphocytes used in the production of hybridoma cells typically are isolated from immunized mammals whose sera have already tested positive for the presence of anti-integrin antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, arninopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-integrin antibodies may be screened by testing the hybridoma culture supernatant for secreted antibodies having the ability to bind to a recombinant integrin-expressing cell line.

To produce antibody homologs, including for example, anti-integrin antibody homologs, that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-integrin antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Fully human monoclonal antibody homologs against, for example integrins, are another preferred binding agent which may block antigens in the method of the invention. In their intact form these may be prepared using in vitro-primed human splenocytes, as described by Boerner et al., 1991, J. Immunol. 147:86–95, "Production of Antigen-specific Human Monoclonal Antibodies from In Vitro-Primed Human Splenocytes".

Alternatively, they may be prepared by repertoire cloning as described by Persson et al., 1991, Proc. Nat. Acad. Sci. USA 88: 2432–2436, "Generation of diverse high-affinity human monoclonal antibodies by repertoire cloning" and Huang and Stollar, 1991, J. Immunol. Methods 141: 227–236, "Construction of representative immunoglobulin variable region CDNA libraries from human peripheral blood lymphocytes without in vitro stimulation". U.S. Pat. No. 5,798,230 (Aug. 25, 1998, "Process for the preparation of human monoclonal antibodies and their use") describes preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 (Aug. 4, 1998, "Transgenic non-human animals for producing heterologous antibodies") describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous, fully human antibody homolog.

Yet another preferred binding agent which may block integrin antigens or fragments thereof in the method of the invention is a humanized antibody homolog having the capability of binding to an integrin protein or fragments thereof. Following the early methods for the preparation of chimeric antibodies, a new approach was described in EP 0239400 (Winter et al.) whereby antibodies are altered by substitution of their complementarity determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to created antibodies which are totally human in composition except for the substituted murine CDRs. Such CDR-substituted antibodies would be predicted to be less likely to elicit an immune response in humans compared to chimeric antibodies because the CDR-substituted antibodies contain considerably less non-human components. The process for humanizing monoclonal antibodies via CDR "grafting" has been termed "reshaping". (Riechmann et al., 1988 Nature 332: 323–327, "Reshaping human antibodies for therapy"; Verhoeyen et al., 1988, Science 239: 1534–1536, "Reshaping of human antibodies using CDR-grafting in Monoclonal Antibodies".

Typically, complementarity determining regions (CDRs) of a murine antibody are transplanted onto the corresponding regions in a human antibody, since it is the CDRs (three in antibody heavy chains, three in light chains) that are the regions of the mouse antibody which bind to a specific antigen. Transplantation of CDRs is achieved by genetic engineering whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in Jones et al., 1986 Nature 321: 522–525, "Replacing the complementarity-determining regions in a human antibody with those from a mouse"; Riechmann, 1988, Nature 332:323–327, "Reshaping human antibodies for therapy"; Queen et al., 1989, Proc. Nat. Acad. Sci. USA 86:10029, "A humanized antibody that binds to the interleukin 2 receptor" and Orlandi et al., 1989, Proc. Natl. Acad. Sci. USA 86:3833 "Cloning Immunoglobulin variable domains for expression by the polymerase chain reaction".

Nonetheless, certain amino acids within framework regions are thought to interact with CDRs and to influence overall antigen binding affinity. The direct transfer of CDRs from a murine antibody to produce a humanized antibody without any modifications of the human V region frameworks often results in a partial or complete loss of binding affinity. In a number of cases, it appears to be critical to alter residues in the framework regions of the acceptor antibody in order to obtain binding activity.

Queen et al., 1989, Proc. Nat. Acad. Sci. USA 86: 10029–10033, "A humanized antibody that binds to the interleukin 2 receptor" and WO 90/07861 (Protein Design Labs Inc.) have described the preparation of a humanized antibody that contains modified residues in the framework regions of the acceptor antibody by combining the CDRs of a murine mAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysts for optimal protein sequence homology to the V region framework of the original murine antibody, in this case, the anti-Tac MAb. In the second step, the tertiary structure of the murine V region is modeled by computer in order to visualize framework amino acid residues which are likely to interact with the murine CDRs and these murine amino acid residues are then superimposed on the homologous human framework. Their approach of employing homologous human frameworks with putative murine contact residues resulted in humanized antibodies with similar binding affinities to the original murine antibody with respect to antibodies specific for the interleukin 2 receptor (Queen et al., 1989 [supra]) and also for antibodies specific for herpes simplex virus (HSV) (Co. et al., 1991, Proc. Nat. Acad. Sci. USA 88: 2869–2873, "Humanised antibodies for antiviral therapy".

According to the above described two step approach in WO 90/07861, Queen et al. outlined several criteria for designing humanized immunoglobulins. The first criterion is to use as the human acceptor the framework from a particular human immunoglobulin that is usually homologous to the non-human donor immunoglobulin to be humanized, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRS.

One may use a different approach (see Tempest, 1991, Biotechnology 9: 266–271, "Reshaping a human monoclonal antibody to inhibit human respiratory syncytial virus infection in vivo") and utilize, as standard, the V region frameworks derived from NEWM and REI heavy and light chains respectively for CDR-grafting without radical introduction of mouse residues. An advantage of using the Tempest et al., 1991 approach to construct NEWM and REI based humanized antibodies is that the 3dimensional structures of NEWM and REI variable regions are known from x-ray crystallography and thus specific interactions between CDRs and V region framework residues can be modeled.

The subject treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

In the methods of the invention the antibodies, including for example, anti-VLA-1 antibody may be administered parenterally. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions of this invention comprise any of the compounds of the present invention, or pharmaceutically acceptable derivatives thereof, together with any pharmaceutically acceptable carrier. The term "carrier" as used herein includes known acceptable adjuvants and vehicles.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents.

The pharmaceutical compositions of this invention may be given orally. If given orally, they can be administered in any orally acceptable dosage form including, but not limited to, capsules, tablets, aqueous suspensions or solutions.

For topical applications, the pharmaceutical compositions may be formulated in a suitable ointment containing the active component suspended or dissolved in one or more carriers.

The pharmaceutical compositions of this invention may also be administered by nasal aerosol or inhalation through the use of a nebulizer, a dry powder inhaler or a metered dose inhaler.

The dosage and dose rate of the compounds of this invention effective to produce the desired effects will depend on a variety of factors, such as the nature of the inhibitor, the size of the subject, the goal of the treatment, the nature of the pathology to be treated, the specific pharmaceutical composition used, and the judgment of the treating physician. Dosage levels of between about 0.001 and about 100 mg/kg body weight per day, preferably between about 0.1 and about 50 mg/kg body weight per day of the active ingredient compound are useful. Most preferably, the antibody homologs will be administered at a dose ranging between about 0.1 mg/kg body weight/day and about 20 mg/kg body weight/day, preferably ranging between about 0.1 mg/kg body weight/day and about 10 mg/kg body weight/day and at intervals of every 1–14 days. In another preferred embodiment the antibody is administered at a dose of about 0.3 to 1 mg/kg when administered I.P. In another preferred embodiment, the antibody is administered at a dose of about 5 to 12.5 mg/kg when administered I.V. Preferably, an antibody composition is administered in an amount effective to provide a plasma level of antibody of at least 1 ug/ml.

Persons having ordinary skill in the art can readily test if an antagonist of the invention is having it intended effect. For instance, cells contained in a sample of the individual's epithelium are probed for the presence of the agent in vitro (or ex vivo) using a second reagent to detect the administered agent. For example, this may be a fluorochrome labelled antibody specific for the administered agent which is then measured by standard FACS (fluorescence activated cell sorter) analysis. Alternatively, presence of the administered agent is detected in vitro (or ex vivo) by the inability or decreased ability of the individual's cells to bind the same agent which has been itself labelled (e.g., by a fluorochrome). The preferred dosage should produce detectable coating of the vast majority of hedgehog-positive cells. Preferably, coating is sustained in the case of an antibody homolog for a 1–14 day period.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I–IV (D. M. Weir and C. C. Blackwell, eds.), 1986; Manipulating the Mouse Embryo, Cold Spring Harbor Laboratory Press, 1986.

The following Examples are provided to illustrate the present invention, and should not be construed as limiting thereof.

EXAMPLES

Chemical Reagents

Fluorescein isothiocyanate (FITC) was purchased from Sigma Chemical Co. (St. Louis, Mo.). Croton oil was purchased from ICN Biochemicals (Aurora, Ohio). Whole sheep blood in Alsevers solution was obtained from East Acres Biologicals (Southbridge, Mass.). Type I rat tail collagen and type IV mouse collagen were purchased from Collaborative Research Inc. (Bedford, Mass.) and Gibco (Gaithersburg, Md.), respectively. Balb/c female mice of 6–8 weeks of age were purchased from Taconic (Germantown, N.Y.) and the $\alpha1\beta1$ integrin-deficient mice on a Balb/c background were as previously described (3).

Example 1

Monoclonal Antibodies. Function-blocking mAbs to murine antigens were prepared in an azide-free and low endotoxin format: Ha31/8 (hamster anti-CD49a; integrin $\alpha1$) (Mendrick et al. 1995. *Lab. Invest.* 72:367–375), Ha1/29 (hamster anti-CD49b; integrin $\alpha2)(\beta1)$ (Mendrick et al. 1995. *Lab. Invest.* 72:367–375; Mendrick, D. L. and D. M. Kelly 1993 *Lab. Invest.* 69:690–702), hamster group II control mAb Ha4/8 (hamster anti-KLH) (Mendrick, D. L. and D. M. Kelly 1993 *Lab. Invest.* 69:690–702), and PS/2 (rat anti-CD49d; integrin $\alpha4\beta1$ chain) (Miyake et al. 1991 *J. Exp. Med.* 173:599–607). In addition, the following function-blocking mAbs to murine antigens were purchased as no-azide/low endotoxin preparations from Pharmingen (San Diego, Calif.): HM$\beta$1-1 (hamster anti-CD29; integrin $\beta1$ chain) (Noto et al. 1995 *Int. Immunol.* 7:835–842), Ha2/5 (hamster anti-CD29; integrin $\beta1$ chain) (Mendrick, D. L. and D. M. Kelly 1993 *Lab. Invest.* 69:690–702), 3E2 (hamster anti-CD54, ICAM-1) (Scheynius et al. 1993 *J. Immunol.* 150:655–663), 5H10-27 (rat anti-CD49e; integrin $\alpha5$) (Kinashi, T., and T. A. Springer. 1994. *Blood Cells.* 20:25–44), GoH3 (rat anti-CD49f; integrin $\alpha6$) (Sonnenberg et al. 1987 *J. Biol. Chem.* 262:10376–10383), and the rat isotype control mAbs R35-95 (rat IgG2a) and R35-38 (rat IgG2b).

Adhesion Assay. Splenocytes from Balb/c mice were cultured with 20 ng/ml IL-2 for 7–12 d. Adhesion of cells to type I and type IV collagen was as previously described (Gotwals et al. 1996 *J. Clin. Invest.* 97:2469–2477). Briefly, 96-well Maxisorp plates (Nunc, Napierville, Ill.) were coated with either 10 µg/ml type IV or 5 µg/ml type I collagen and non-specific sites blocked with 1% BSA. IL-2 activated splenocytes were labeled with 2 µM BCECF [2',7'-bis(carboxyethyl)-5(6) carboxyl fluorescein penta acetoxymethylester] (Molecular Probes, Eugene, Oreg.) and incubated with 10 µg/ml of indicated mAbs for 15 min. $10^5$ cells in 0.25% BSA in RPMI were then added to coated wells and incubated for 60 min at 37° C. Unbound cells were removed by washing three times with 0.25% BSA in RPMI. Adhesion was quantified using a CytoFluor 2350 fluorescent plate reader (Millipore, Bedford, Mass.). The ratio of bound cells to input cells was measured and percent adhesion relative to control mAb-treated cells (normalized to 100%) calculated. Background values due to cell adhesion on wells coated with BSA alone were subtracted.

Figure 1B:
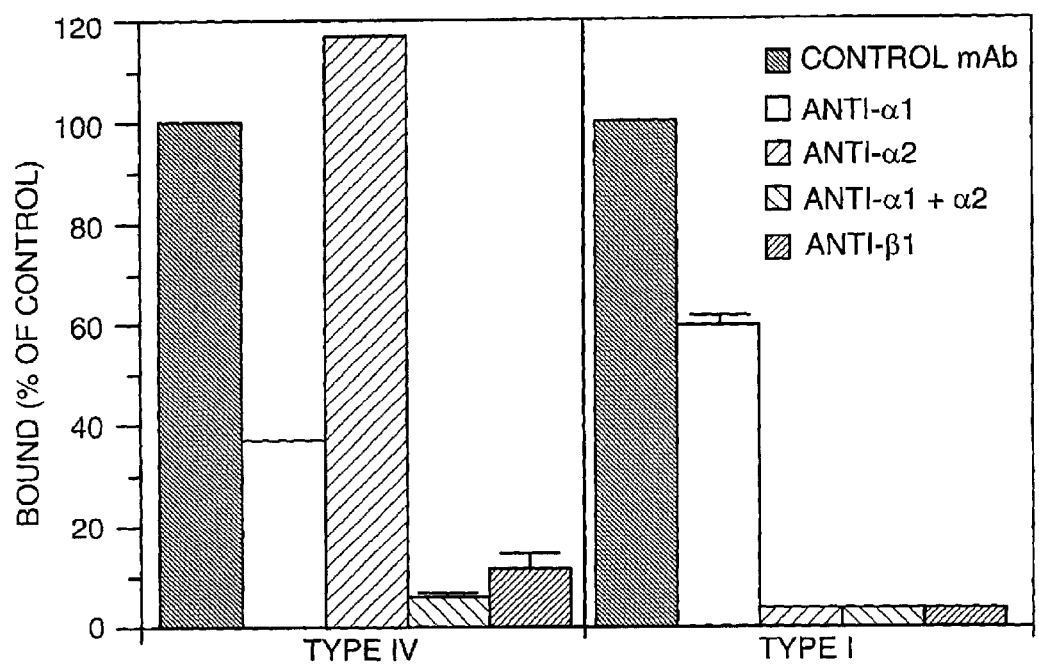

Expression and functional blockade of $\alpha1\beta1$ and $\alpha2\beta1$ on activated leukocytes. Given the key role leukocytes play in inflammation, we decided to test whether anti-$\alpha1$ and anti-$\alpha2$ mAbs were capable of blocking leukocyte adhesion to collagens. In order to obtain leukocytes expressing high levels of both $\alpha1$ and $\alpha2$, murine T cells were stimulated in vitro with IL-2 for 7–12 d. These cells expressed high levels of both $\alpha1$ and $\alpha2$ (FIG. 1A), and bound well to both collagen type IV and type I-coated surfaces (FIG. 1B). Adhesion to type IV collagen was partially inhibited by anti-$\alpha1$ mAb alone and was not inhibited by anti-$\alpha2$ mAb alone. In contrast, adhesion to type I collagen was completely inhibited by anti-$\alpha2$ mAb and anti-$\alpha1$ mAb alone showed only partial inhibition. Both anti-$\beta1$ mAb and the combination of anti-$\alpha1$ and anti-$\alpha2$ mAbs completely inhibited adhesion to types I and IV collagen. Having demonstrated that the $\alpha1\beta1$ and $\alpha2\beta1$ integrins are expressed on activated T cells and that anti-$\alpha1$ and $\alpha2$ mAbs are able to functionally block leukocyte adhesion to collagens, we used these mAbs to investigate the in vivo role of these integrins in animal models of inflammatory disorders.

Example 2

Inhibition of DTH responses by anti-integrin mAbs. SRBC-induced delayed type hypersensitivity (DTH) responses were adapted from a previously published protocol (Hurtrel et al. 1992 *Cell. Immunol.* 142:252–263). Briefly, mice were immunized s.c. in the back with $2 \times 10^7$ SRBC in 100 ul PBS on d 0. The mice were challenged on d 5 by injecting $1 \times 10^8$ SRBC in 25 ul PBS s.c into the right hind footpad. Footpad thickness was measured with an engineer's caliper (Mitutoyo/MTI, Paramus, N.J.) 20 h after antigen challenge, and the degree of footpad swelling calculated. Results are reported as the mean percent increase footpad thickness±SEM and calculated as % increase=[1−(Right footpad thickness 20 h after antigen challenge/Uninjected left footpad thickness 20 h after antigen challenge)]×100. To block the effector phase of the SRBC-induced DTH response, therapeutic or control mAb (100 ug), which were prepared according to the methods described in Example 1, was given i.p. 1 h prior to antigen challenge on d 5.

Figure 2:
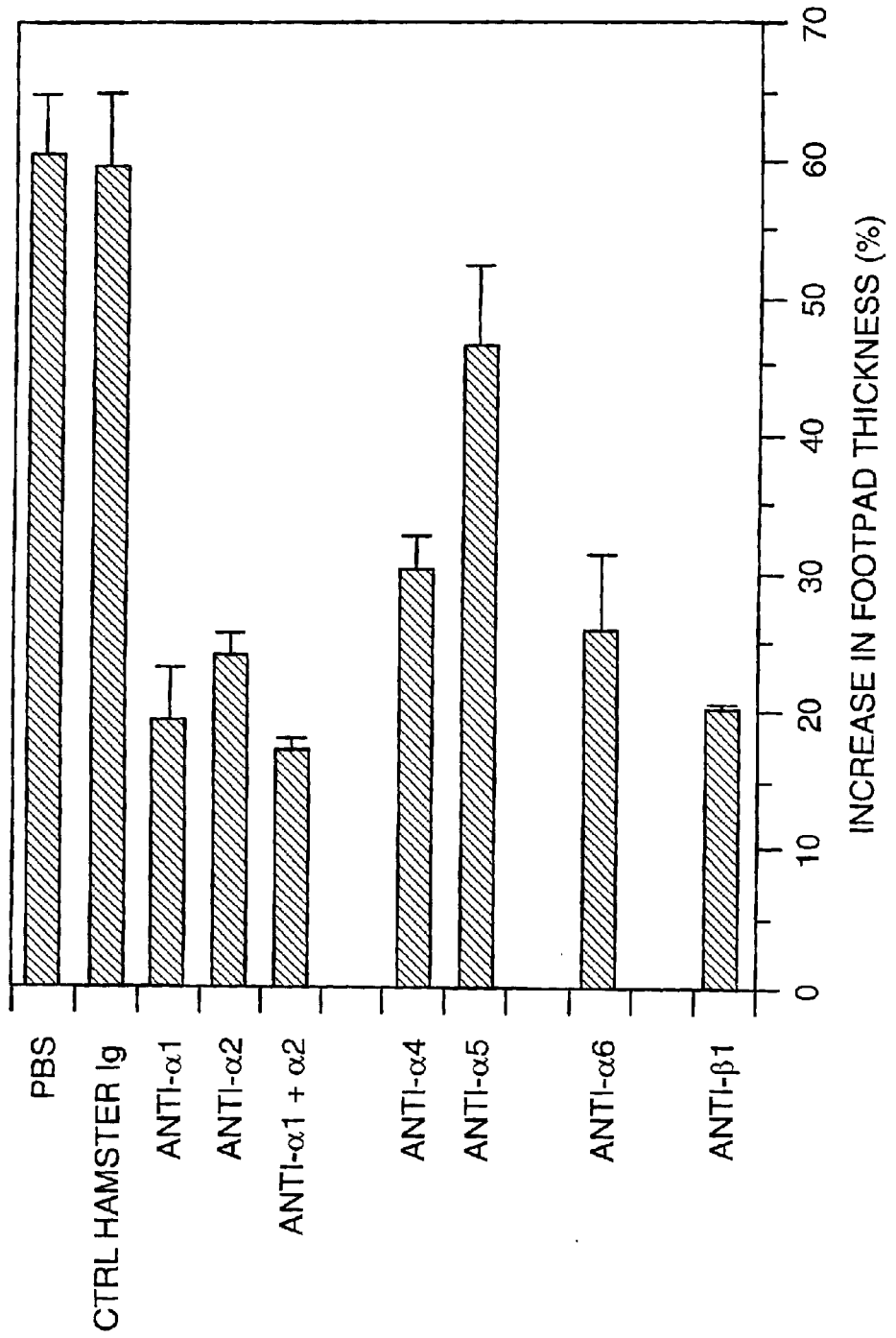
FIG. 2. Effect of anti-integrin mAbs on the effector phase of delayed-type hypersensitivity. SRBC-sensitized mice were injected i.p. with the indicated mAbs 1 h prior to SRBC challenge. Footpad thickness was measured 20 h after antigen challenge, and results shown as % increase in footpad thickness±SEM as illustrated in Example 2. These data represent a summary of eight experiments with n=79 (PBS), 68 (control hamster Ig), 68 (anti-α1), 29 (anti-α2), 18 (anti-α1+anti-α2), 45 (anti-α4), 18 (anti-α5), 20 (anti-α6), and 10 (anti-β1). The mAbs used were: Ha4/8 (control hamster Ig group 2), Ha31/8 (anti-α1), Ha1/29 (anti-α2), PS/2 (anti-α4), 5H10-27 (anti-α5), GoH3 (anti-α6), and HMβ1-1 (anti-β1).

SRBC-induced DTH is a well characterized in vivo model of inflammation, and in particular psoriasis, that has been used to demonstrate the importance of a variety of cytokines and adhesion molecules in inflammation (Tedder et al. 1995 *J. Exp. Med.* 181:2259–2264, Terashita et al. 1996 *J. Immunol.* 156:4638–4643). SRBC-sensitized mice received anti-integrin mAbs 1 h prior to footpad antigen challenge and inflammation was assessed 20 h later as measured by increased footpad thickness. PBS and control hamster Ig-treated mice showed a 60–70% increase in footpad thickness 20 h after antigen challenge (FIG. 2). Compared to control hamster Ig treatment, anti-$\alpha$1 or anti-$\alpha$2 mAbs resulted in a 68% and 60% inhibition in footpad thickness, respectively. The combination of anti-$\alpha$1 and $\alpha$2 mAbs resulted in 71% inhibition, demonstrating little additive effect over anti-$\alpha$1 or anti-$\alpha$2 mAbs alone. Treatment with other anti-integrin mAbs was also effective at inhibiting DTH effector response. The degree of inhibition seen with the various mAb treatments was 49% (anti-$\alpha$4), 23% (anti-$\alpha$5), and 57% (anti-$\alpha$6). Lastly, mAb blockade of the common $\beta$1 integrin subunit (mAb HMBI-1) inhibited the effector DTH response by 67%.

Example 3

Inhibition of CHS effector responses by anti-integrin mAbs. Contact hypersensitivity (CHS) to FITC was assayed as previously described (Gaspari et al. 1991 In Current Protocols in Immunology. J. E. Coligan, A. M. Kruisbeek, D. H. Margulies, E. M. Shevach, and W. Strober, editors. John Wiley & Sons, New York. Section 4.2:1). Briefly, mice were sensitized by painting 100 ul 0.5% FITC in 1:1 acetone/dibutylphthalate onto the shaved back on d 0. 10 d later, animals were challenged by applying 5 ul 0.5% FITC onto both sides of each ear. Ear swelling response was determined by ear thickness measured with an engineer's caliper (Mitutoyo/MTI, Paramus, N.J.) at the time of antigen challenge (d 10) and 24 h later, and the results reported as mean percent increase in baseline ear thickness±SEM. Increase in ear thickness was calculated as % increase=[1−(Ear thickness 24 h after antigen challenge/Ear thickness at the time of antigen challenge)]×100. To block the effector phase of the CHS response, therapeutic or control mAb (250 ug) was given i.p. 4 h prior to antigen challenge on d 10. Mice that were antigen-sensitized and ear challenged with vehicle only (vehicle control) or mice that were ear challenged without prior sensitization (irritant control) served as negative controls (never exceeded 2% increase in ear thickness).

Figure 3:
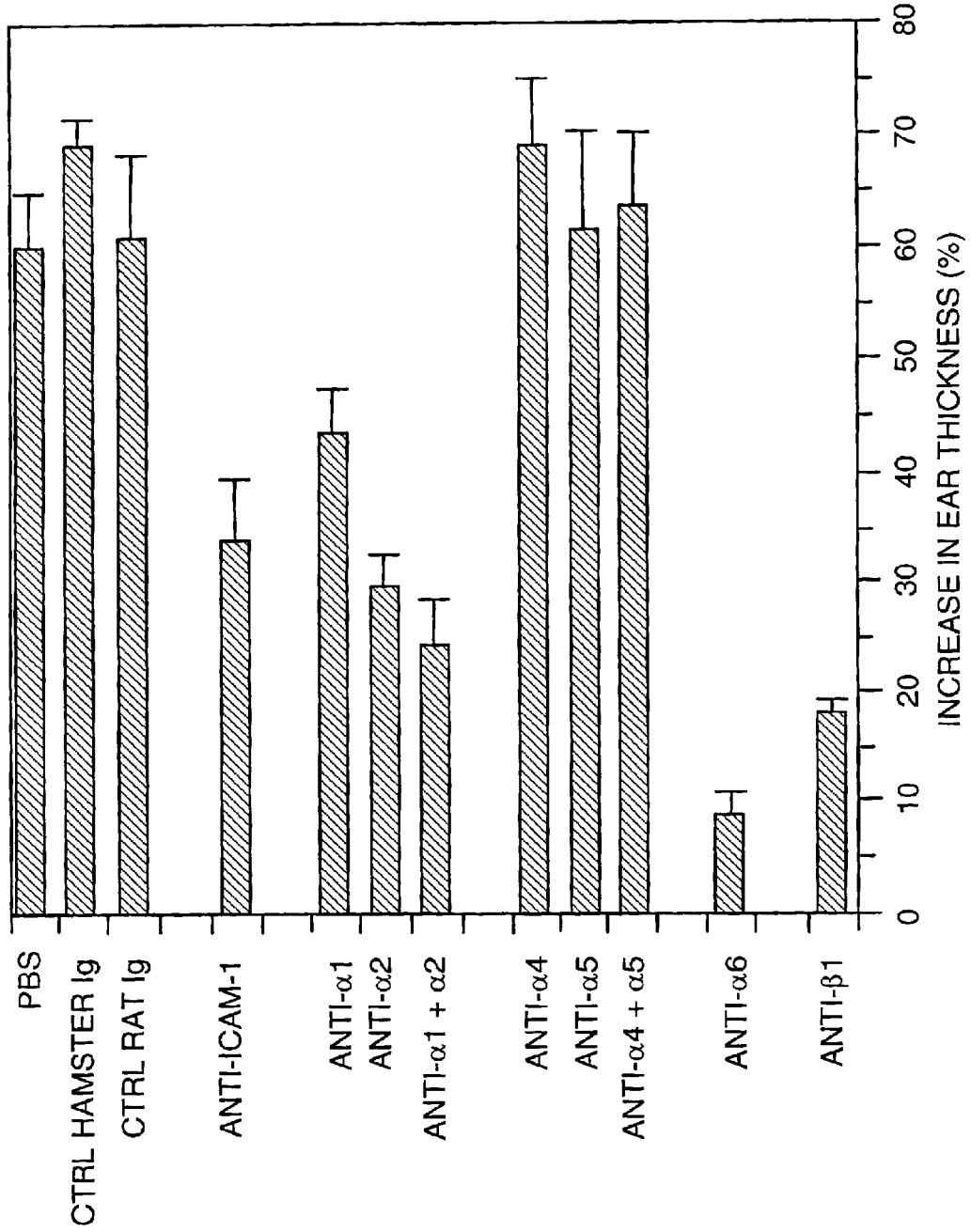
FIG. 3. Effect of anti-integrin mAbs on the effector phase of contact hypersensitivity. FITC-sensitized mice were injected i.p. with the indicated mAbs 4 h prior to FITC challenge. Ear thickness was measured at baseline and 24 h later, and results shown as % increase in ear thickness±SEM as illustrated in Example 3. These data represent a summary of nine experiments with n=74 (PBS), 60 (control hamster Ig), 26 (anti-ICAM-1), 44 (anti-α1), 44 (anti-α2), 38 (anti-α1+anti-α2), 36 (anti-α4), 16 (anti-α5), 26 (anti-α4+anti-α5), 24 (anti-α6), and 22 (anti-β1). The hamster mAbs used were: Ha4/8 (control hamster Ig group 2), Ha31/8 (anti-α1), Ha1/29 (anti-α2), HMβ1-1 (anti-β1), 3E2 (anti-ICAM-1); the rat mAbs used were: R35-95 and R35-38 (control rat IgG2a and rat IgG2b, respectively), PS/2 (anti-α4), 5H10-27 (anti-α5), GoH3 (anti-α6).

Given that CHS is mechanistically distinct from DTH and involves different effector cells, we investigated what effect anti-integrin mAbs had on the effector phase of the CHS response. Mice were hapten-sensitized using FITC applied to their shaved backs, followed 10 d later with FITC challenge to the ear resulting in an inflammatory response the next day. FITC-sensitized mice demonstrated a 60–70% increase in thickness 24 h after antigen challenge (FIG. 3). Consistent with published results (Scheynius et al. J. Immunol. 150:655–663), anti-ICAM-1 mAb treatment resulted in 51% inhibition of ear swelling. Compared to control hamster mAb, treatment of mice with anti-$\alpha$1 or anti-$\alpha$2 mAb 4 h prior to antigen challenge resulted in 37% and 57% inhibition in ear swelling, respectively (FIG. 3). The combination of anti-$\alpha$1 and anti-$\alpha$2 mAbs resulted in slightly greater inhibition of ear swelling (65%). Treatment with other mAbs to $\beta$1 integrins revealed that while anti-$\alpha$4 and anti-$\alpha$5 mAbs resulted in no inhibition of FITC-induced CHS effector response when compared to control rat mAb, treatment with anti-$\alpha$6 mAb resulted in an 86% inhibition of effector responses. Lastly, mAb blockade of the common $\beta$1 integrin subunit inhibited CHS effector responses by 74%. Similar CHS results were obtained using different strains of mice (C57/BL6, 129/Sv) and a different sensitizing agent (oxazolone) (data not shown). Similar to the results seen in the SRBC-induced DTH model, histologic analysis of inflamed ears revealed that both edema formation and leukocytic infiltration were inhibited by anti-$\alpha$1 and anti-$\alpha$2 mAb treatment.

Consistent with the finding that $\alpha$1$\beta$1 and $\alpha$2$\beta$1 can be expressed on IL-2-activated splenocytes, analysis of lymph nodes from antigen-sensitized mice (FITC or oxazolone) revealed $\alpha$1$\beta$1 and $\alpha$2$\beta$1 to be expressed exclusively on CD44$^{hi}$ LFA-1$^{hi}$ activated CD4+ and CD8+ T cells (data not shown). Treatment of mice with anti-$\alpha$1 and anti-$\alpha$2 mAbs did not result in deletion of these cells, as the numbers of activated T cells in both spleen and lymph nodes seen in response to antigen sensitization in the CHS model was unaffected. In addition, effector cells were not functionally deleted as prolonged treatment of antigen-sensitized mice with anti-$\alpha$1 and anti-$\alpha$2 mAbs (d 10–16) did not affect the inflammatory response of mice challenged with antigen at d 20 (data not shown).

Example 4

Figure 4:
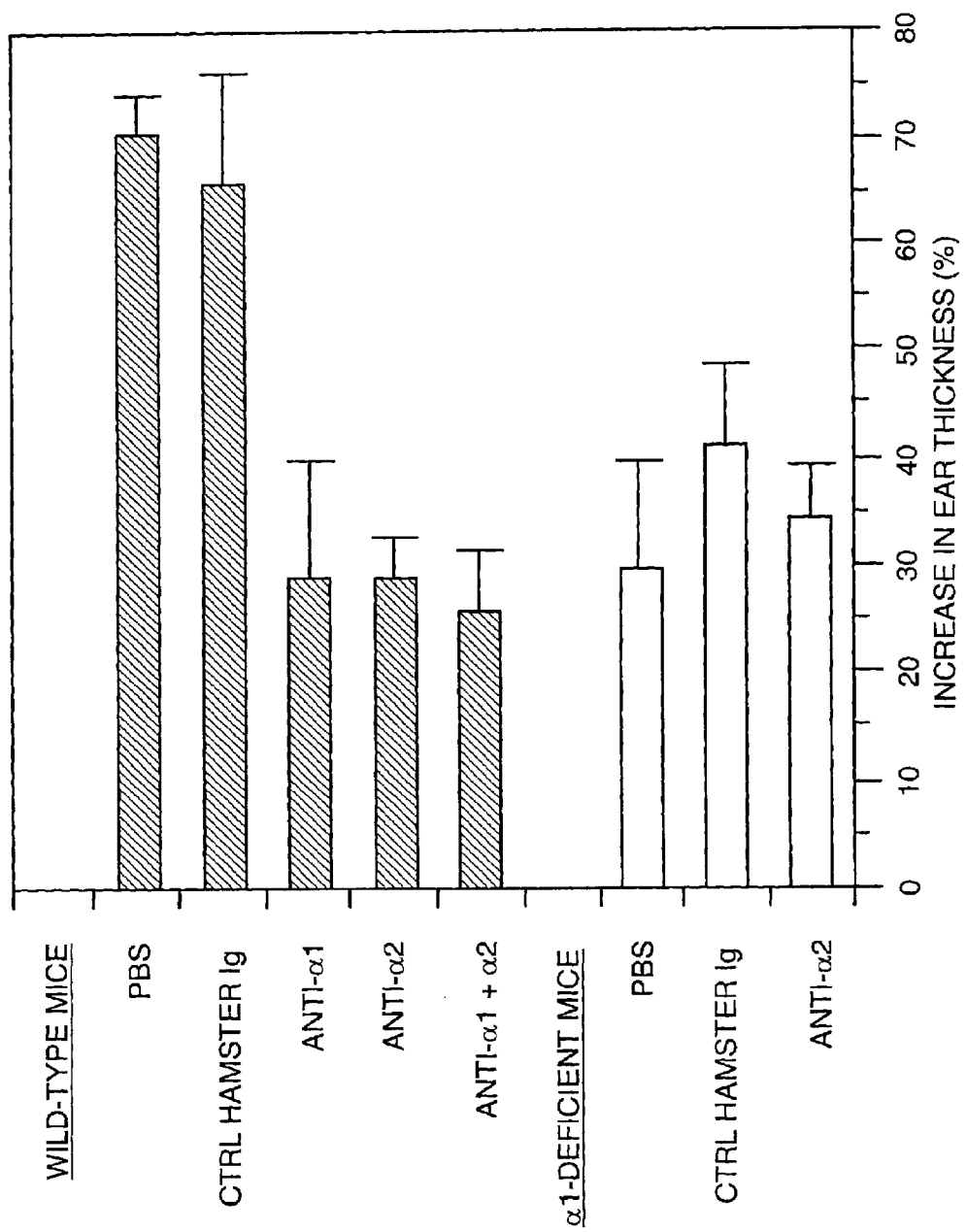
FIG. 4. Contact hypersensitivity responses in α1-deficient mice compared to wild-type mice. FITC-sensitized mice were injected i.p. with indicated mAbs 4 h prior to FITC challenge. Ear thickness was measured at baseline and 24 h later, and results shown as % increase in ear thickness±SEM as illustrated in Example 4. Groups of four to five mice per condition were used, and all experiments were performed a minimum of three times. One representative experiment is shown.

CHS effector responses are decreased in $\alpha$1$\beta$1-deficient mice. To exclude the possibility that the inhibitory role of $\alpha$1$\beta$1 in the effector response of FITC-mediated CHS was mAb-mediated, experiments were carried out in wild-type and $\alpha$1$\beta$1-integrin deficient mice (FIG. 4). MAb inhibition of the effector phase in wild-type mice was consistent with previous results, with 56% inhibition in ear thickness seen with anti-$\alpha$1, 56% with anti-$\alpha$2, and 62% with a combination of anti-$\alpha$1 and anti-$\alpha$2. The effector phase of CHS was significantly reduced in untreated $\alpha$1$\beta$1-deficient mice as compared to untreated wild-type mice (30% vs 71% increase in ear thickness, respectively). As expected, the level of ear swelling in untreated $\alpha$1$\beta$1-deficient mice was equivalent to the level of ear swelling seen in anti-$\alpha$1 mAb-treated wild-type mice. Lastly, mAb blockade of $\alpha$2$\beta$1 in the $\alpha$1$\beta$1-deficient mice resulted in only slightly increased inhibition of ear swelling, consistent with the results seen in wild-type mice treated with a combination of anti-$\alpha$1 and anti-$\alpha$2 mAbs.

Example 5

To further exclude the possibility that the inhibitory effect of the anti-integrin mAbs seen in both the DTH and CHS models of inflammation is caused by a general anti-inflammatory effect mediated by the anti-$\alpha$1 and anti-$\alpha$2 mAbs, the effect of these mAbs on irritant dermatitis was studied.

To assess irritant dermatitis, mice were painted with 5 ul of 0.8% croton oil in acetone on both sides of each ear. Therapeutic or control antibodies were given 4 h prior to the application of the irritant. Ear swelling was measured 24 h later as described above and compared to ear thickness prior to croton oil application. Results are reported as mean percent increase in baseline ear thickness±SEM as described above. Mice painted with acetone only (vehicle control) served as a negative control.

Figure 5:
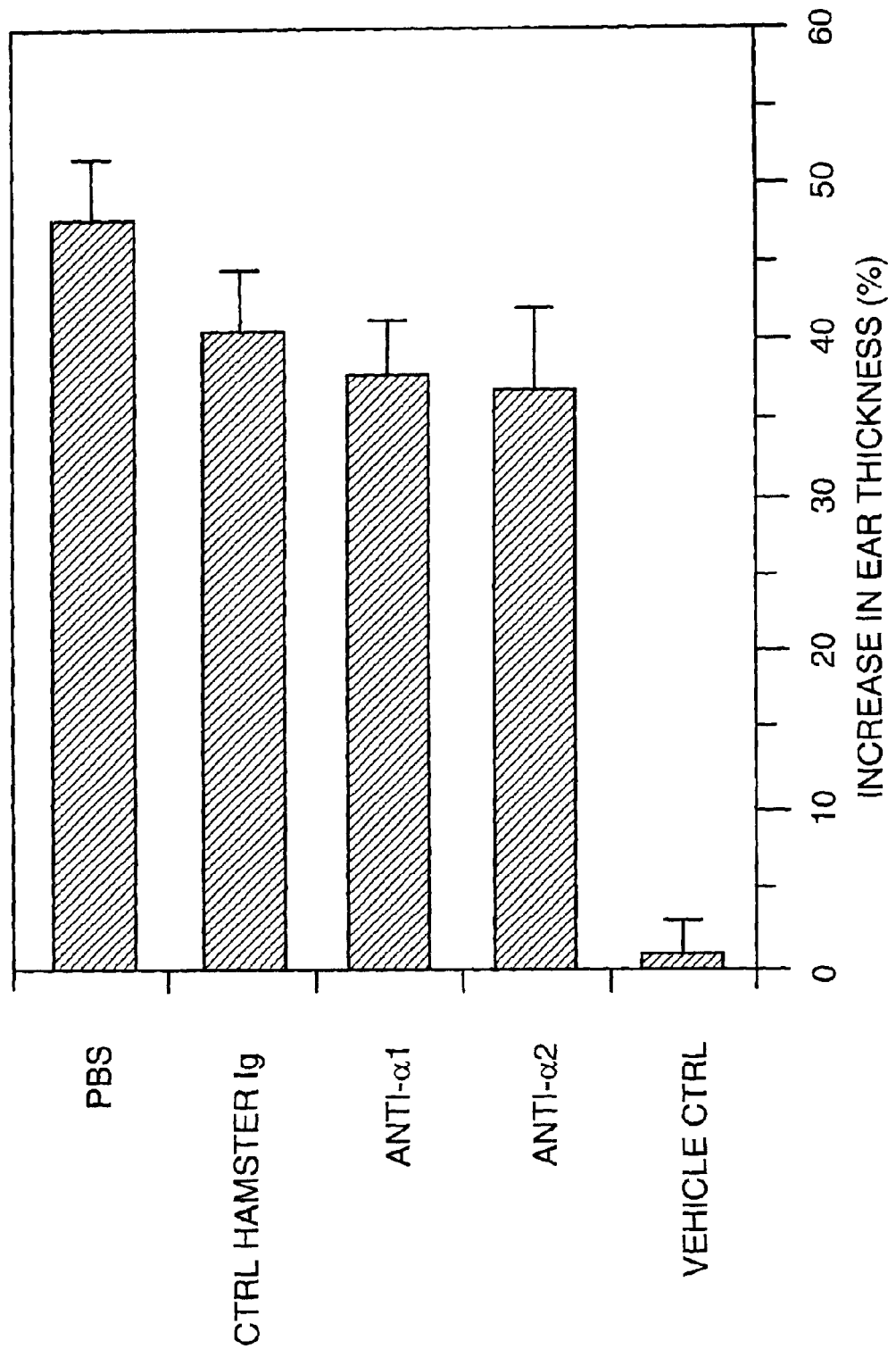
FIG. 5. Effect of anti-α1 and anti-α2 mAbs on croton oil-induced non-specific inflammation. Mice were injected i.p. with indicated mAbs 4 h prior to ear painting with croton oil. Ear thickness was measured at baseline and 24 h later, and results shown as % increase in ear thickness±SEM as illustrated in Example 5. Groups of four to five mice per condition were used, and all experiments were performed a minimum of three times. One representative experiment is shown.

24 h later, ears of mice treated with croton oil showed a significant increase in ear thickness (48%), when compared to mice receiving vehicle only (acetone). Toxic ear swelling caused by croton oil was not significantly affected in mice pretreated with anti-α1 or anti-α2 mAbs when compared to either PBS or control mAb-treated animals (FIG. 5). Histologic examination of the croton oil-treated ears revealed no differences in numbers or types of infiltrating cells or edema formation in mice treated with anti-α1 or anti-α2 mAbs, as compared to control mAb-treated mice or PBS-treated mice (data not shown).

Example 6

Inhibition of arthritis by α1β1 and α2β1. As α1β1 is well expressed on infiltrating cells in the synovium of arthritis patients, we decided to examine whether anti-α1 or anti-α2 mAbs would be inhibitory in an accelerated model of arthritis previously described (Terato et al. 1992 *J. Immunol.* 148:2103–2108; Terato et al. 1995 *Autoimmunity.* 22:137–147).

Figure 6:
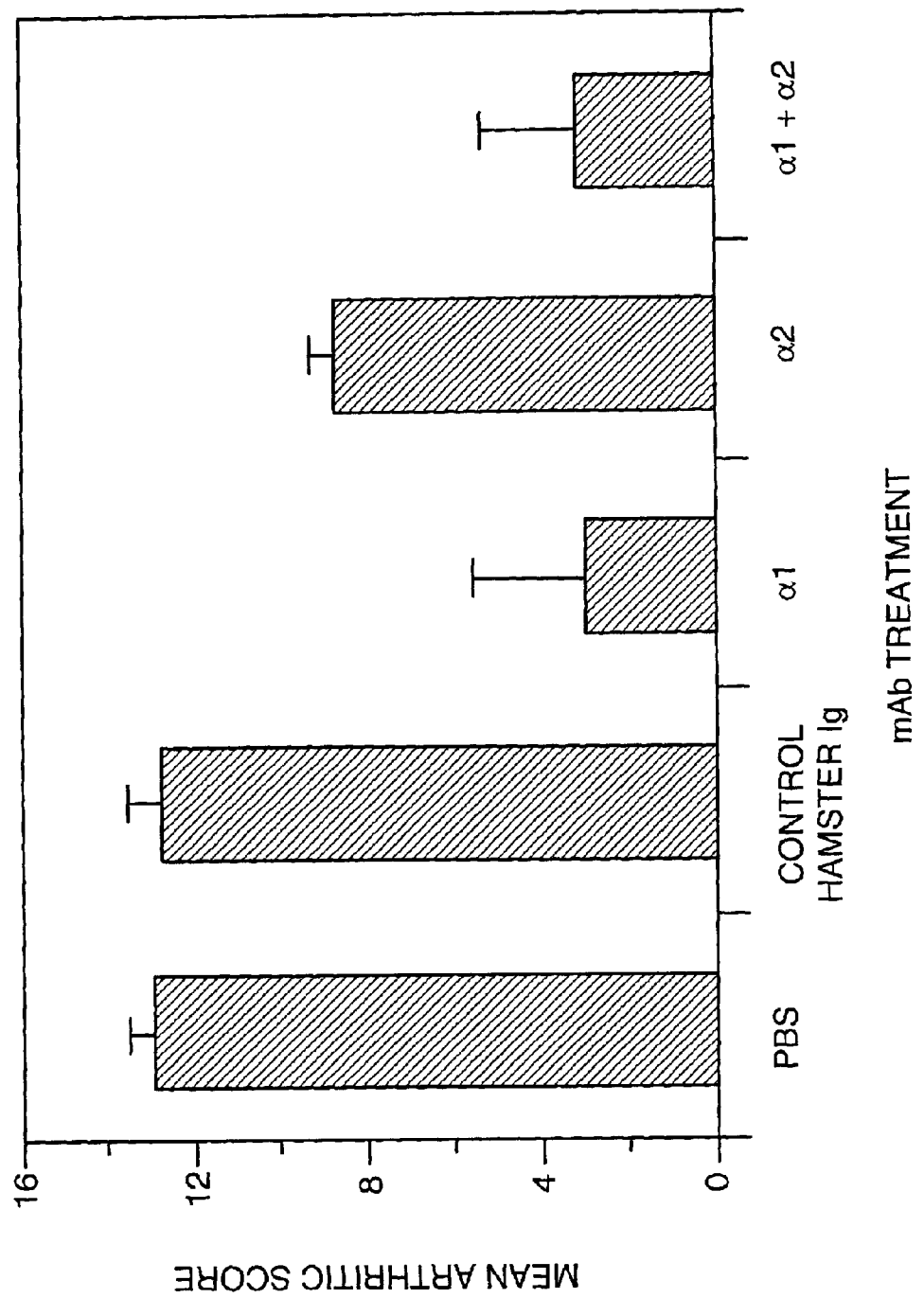
FIG. 6. Effect of anti-α1 and α2 mAbs in collagen mAb-induced arthritis. Mice were injected i.p. with anti-collagen mAbs at d 0, followed by LPS on day 3. Mice were injected i.p. with indicated mAbs every $3^{rd}$ day starting on d 0. Clinical arthritis was apparent 2–3 d following LPS injection and continued for several weeks. Each limb was evaluated on a 0 to 4 scale every $3^{rd}$ day as illustrated in Example 6 and results are expressed as the mean arthritic score between d 9 and d 15 (±SEM) of all four limbs. These data represent a summary of four experiments with each experiment consisting of groups of three to four mice per condition.

Arthrogen-CIA Antibody kits were purchased from Stratagene (La Jolla, Calif.) and arthritis induced using a well established protocol (Terato et al. 1992 *J. Immunol.* 148:2103–2108; Terato et al. 1995 *Autoimmunity.* 22:137–147). Briefly, arthritis was induced through i.p. injection of a cocktail of 4 anti-collagen type II mAbs (1 mg each) on d 0, followed by i.p. injection of 50 ug LPS on d 3. Over the course of the next 3–4 d, the mice developed swollen wrists, ankles and digits. Therapeutic or control mAb (250 ug) was administered i.p. 4 h prior to injection of the anti-collagen mAbs on d 0, and again 4 h prior to LPS administration on d 3, and then continuing every $3^{rd}$ day for the length of the experiment. Beginning on d 3, mice were evaluated for the development of arthritis. Severity of arthritis in each limb was scored using a four point system. 0=normal; 1=mild redness, slight swelling of ankle or wrist; 2=moderate swelling of ankle or wrist; 3=severe swelling including some digits, ankle, and foot; 4=maximally inflamed. Severe arthritis in Balb/c mice developed within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 6). In contrast, treatment with anti-α1 mAb alone resulted in a marked reduction (78%) in arthritis, lasting the duration of the experiment. Treatment with anti-α2 mAb alone also had a beneficial effect, resulting in a 32% decrease in the arthritic score as compared to control mAb-treated mice. The combination of anti-α1 and anti-α2 mAbs resulted in a similar degree of inhibition as seen with anti-α1 mAb alone.

Example 7

Figure 7:
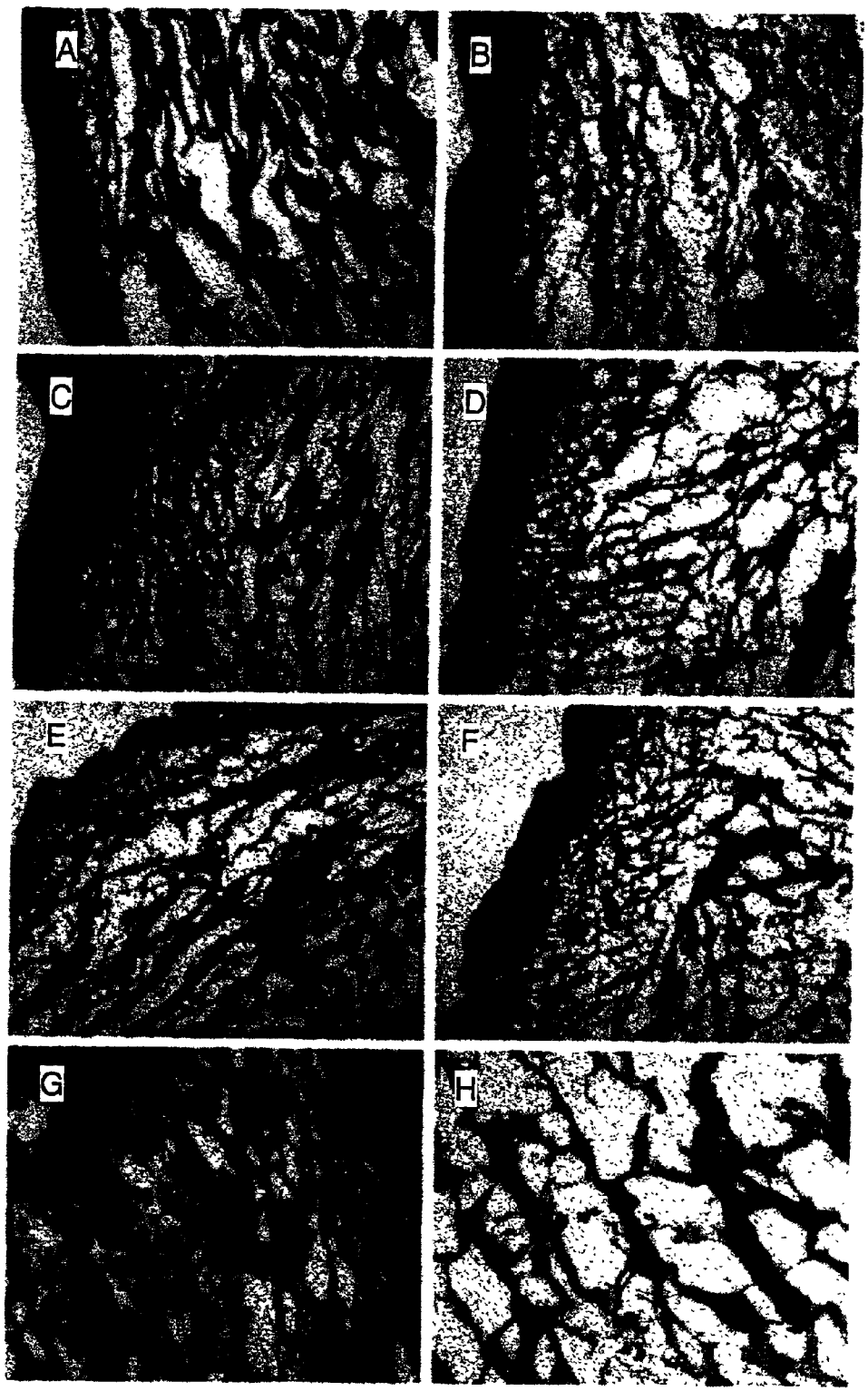
FIG. 7. Administration of anti-α1 or anti-α2 mAbs inhibits leukocyte infiltration into footpads during a DTH response. The experiment was performed as described in FIG. 2. Footpads were excised 20 h following antigen challenge and tissue sections stained with hematoxylin and eosin. Tissue sections are from footpads of either unchallenged mice (A) or SRBC-sensitized mice challenged with SRBC (B–H). Mice were treated 1 h prior to challenge with either PBS (B), control hamster Ig (C, G), anti-α1 (D), anti-α2 (E) or a combination of anti-α1 and anti-α2 mAbs (F,H). Magnification: ×100 (A–F), ×400 (G–H).

Histological analysis of effect of anti-α1 and anti-α2 mAb treatment on the inflammatory cellular infiltrate. Further histological analysis of the SRBC-induced DTH response confirmed the ability of anti-α1 and anti-α2 mAb treatment to modulate the elicited inflammatory response (FIG. 7). An unchallenged footpad from an SRBC-sensitized mouse (FIG. 7 Panel A) showed virtually no inflammatory cellular infiltrate when compared to an SRBC-challenged footpad from the same mouse (FIG. 7 Panel B). Treatment of SRBC-sensitized mice with anti-α1 and anti-α2 mAbs either alone or combined greatly reduced the number of these infiltrating cells found in SRBC-challenged footpads when compared to control mAb-treated mice (FIG. 7 Panel C-F). Closer examination of the infiltrating cells revealed most cells to be composed of neutrophils, with some monocytes and lymphocytes present, and confirmed that anti-α1 and anti-α2 mAb treatment greatly decreased the numbers of these cells (FIG. 7 Panel G-H).

Example 8

Figure 8A:
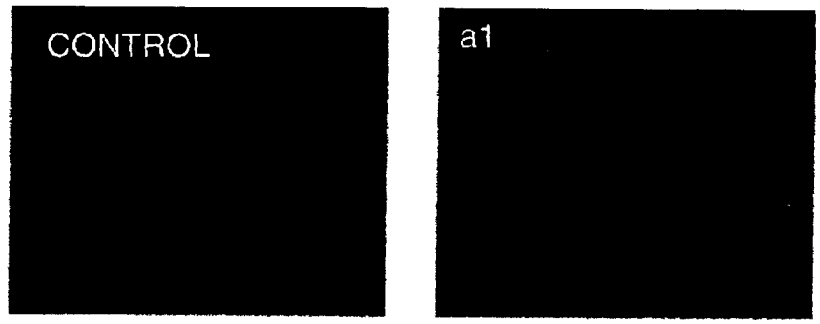
FIG. 8. α1β1 is expressed on infiltrating leukocytes in footpads during a DTH response. Immunohistochemical staining of infiltrating leukocytes from an untreated inflamed footpad 20 h after antigen challenge. (A). Serial sections stained directly with Alexa488-conjugated control mAb and anti-α1 mAb. (B). Dual immunofluorescent staining with Alexa488-conjugated anti-α1 mAb and Phycoerythrin (PE)-conjugated cell lineage-specific mAbs. PE-conjugated mAbs utilized were specific for granulocytes/monocytes (anti-CD11b), neutrophils (anti-Ly6G/Gr-1), and T lymphocytes (anti-CD3). Magnification: ×400.
Figure 8B:
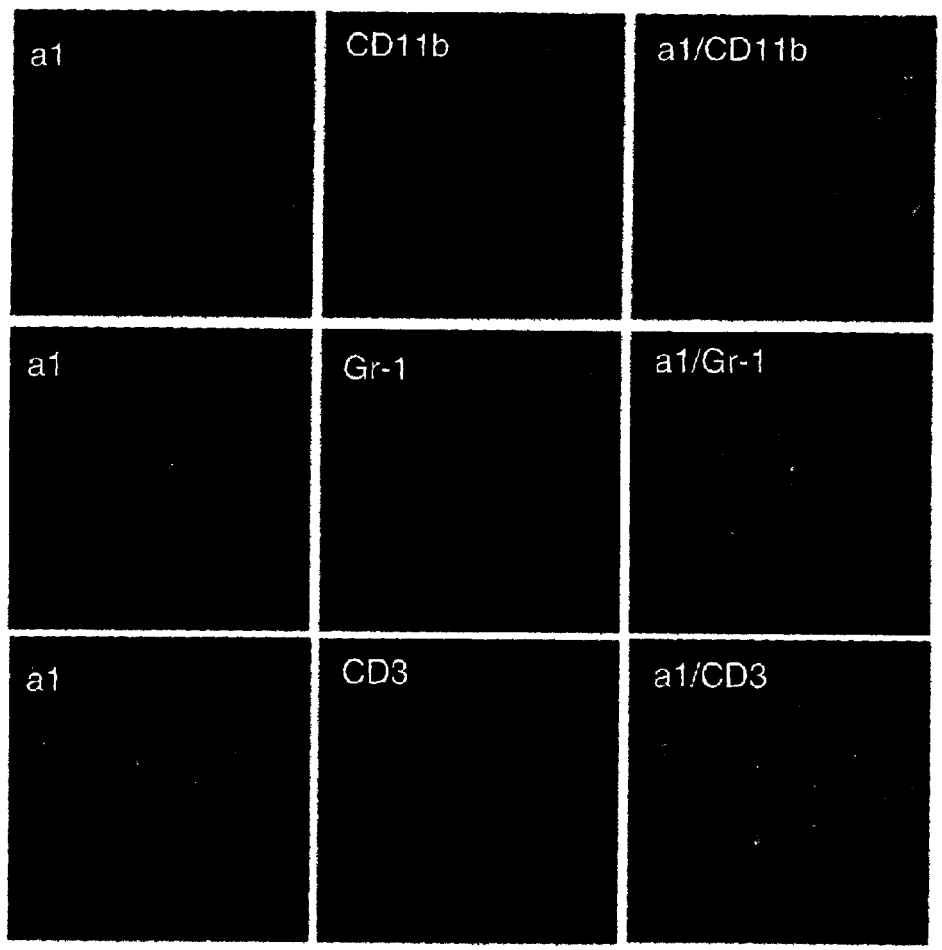

Immunohistochemical demonstration of α1-expressing cells in the inflammatory cellular infiltrate. Immunohistochemistry was performed to more precisely determine the nature of the infiltrating cells and whether they express collagen-binding integrins (FIG. 8). Infiltrating cells from an inflamed footpad of an untreated mouse were examined for expression of α1β1 integrin and cell lineage markers (FIG. 8). α1β1 integrin was found to be expressed on many infiltrating leukocytes (FIG. 8A). Dual immunohistochemistry was utilized to identify the nature of the infiltrating cells and the distribution of α1β1 expression (FIG. 8B). Using cell lineage markers, the infiltrate was found to be if composed largely of granulocyte/monocytes (Mac-1+), with many of these cells being neutrophils (Gr1+), along with a smaller number of T lymphocytes (CD3+) (FIG. 8B). Expression of α1β1 integrin was found among all three subsets of cells, with α1 expressed on a subset of Mac-1+ granulocyte/monocytes, a subset of Gr1+ neutrophils, and on the majority of infiltrating CD3+ T lymphocytes (FIG. 8B). Detailed immunohistochemical analysis revealed that although anti-α1 and anti-α2 mAb treatment reduced the numbers of infiltrating cells, no change in the cellular composition of the infiltrate was seen (data not shown). Immunohistochemistry staining with a FITC anti-hamster mAb confirmed the ability of the anti-α1 and anti-α2 mAb to localize to the inflamed footpad (data not shown).

Example 9

Figure 9:
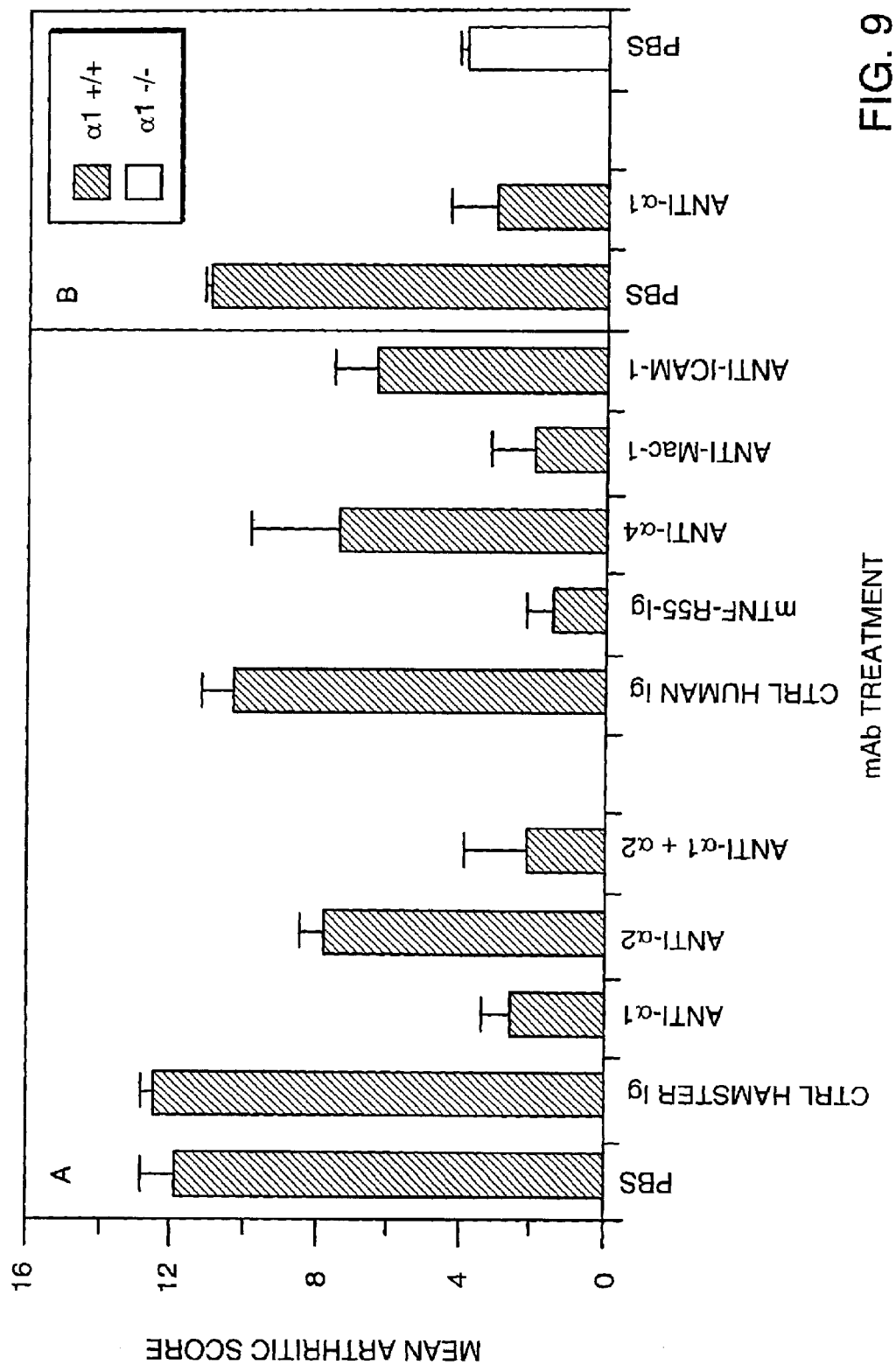
FIG. 9. Effect of anti-α1 and α2 mAbs in collagen mAb-induced arthritis. (A). Preventative treatment of mice with either anti-α1 or anti-α2 mAb decreases arthritic score. Mice were treated with anti-collagen mAbs at d 0, followed by LPS on d 3. Arthritis was apparent by d 6 and continued for several weeks. Mice were treated with the indicated mAbs every $3^{rd}$ day starting on d 0. Each limb was evaluated and scored on a 0 to 4 scale every $3^{rd}$ day. Results are expressed as the mean arthritic score between d 9 and d 15 (±SEM) of all four limbs (maximum score of 16). Groups of 4 mice per condition were used; the average of 12 experiments is shown. (B). α1-deficient mice have a reduced arthritic score comparable to anti-α1 mAb-treated wild-type mice. Experimental details and scoring are as outlined above. Groups of 4 mice per condition were used; the average of 2 experiments is shown.

Inhibition of arthritis by mAbs to α1β1 and α2β1 and in α1-deficient mice. As α1β1 is well expressed on infiltrating cells in the synovium of arthritis patients, we decided to examine whether anti-α1 or anti-α2 mAbs would be inhibitory in an accelerated model of arthritis previously described (Terato et al. 1992 *J. Immunol* 148:2103–2108; Terato et al. 1995 *Autoimmunity* 22:137–147). This model involves injection of a cocktail of anti-collagen type II mAbs into mice, followed later by LPS administration, resulting in the development of arthritis over the next 3–7 d. Mice were given mAb every $3^{rd}$ day starting at d 0, and scored for the development of arthritis every $3^{rd}$ day. Severe arthritis developed in all mice within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 9A). In contrast, treatment with anti-α1 mAb alone resulted in a marked reduction (79% and higher) in arthritis, lasting the duration of the experiment. Treatment with anti-α2 mAb alone also had a beneficial effect, resulting in a 37% decrease in the arthritic score as compared to control mAb-treated mice. The combination of anti-α1 and anti-α2 mAbs resulted in a similar degree of inhibition as seen with anti-α1 mAb alone. Reduction of arthritic score with anti-α1 mAb treatment was seen in all mice and compares favorably with several other mAb-based treatments for arthritis such as soluble TNF receptor Ig fusion protein (Mori et al. 1996 *J. Immunol.* 157:3178–3182), anti-Mac-1 (Taylor et al. 1996 *Immunology.* 88:315–321), anti-(α4 (Seiffge 1996 J. Rheumatol. 23:2086–2091), and anti-ICAM-1 (Kakimoto et al.

1992 Cell Immunol. 142:326–337) (FIG. 9A). In agreement with mAb-based data showing an important role for α1β1 in arthritis, untreated α1-deficient mice showed significant reduction in arthritic score when compared to wild-type mice (FIG. 9B).

Example 10

Figure 10:
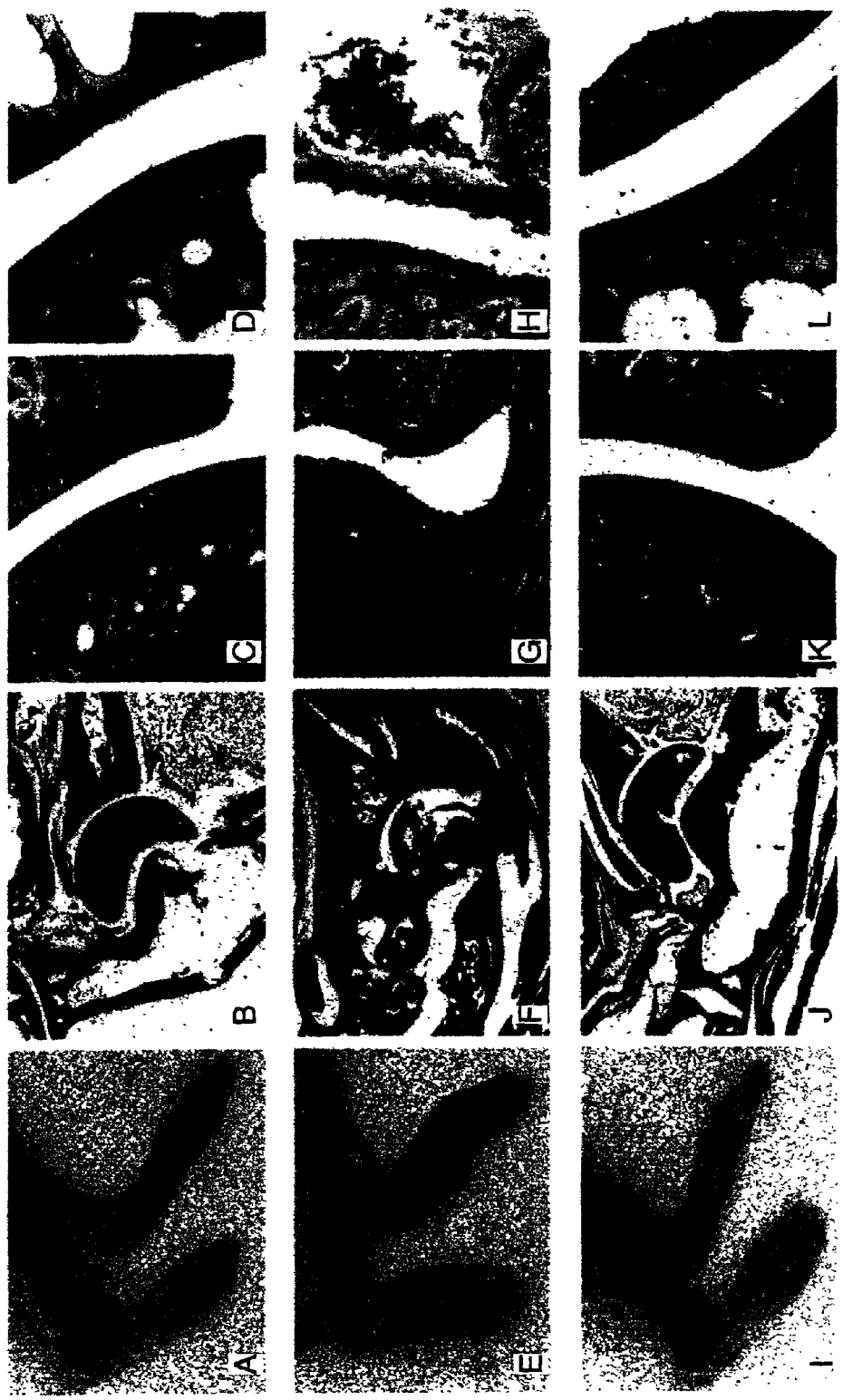
FIG. 10. Effect of anti-α1 mAb treatment on the immunopathology of arthritic joints. Anti-α1 mAb treatment reduces leukocytic infiltration, adherence of cells to joint surfaces, and cartilage destruction as evidenced by proteoglycan loss. Hind limbs from normal mice (A–D) or arthritic mice (d 8) receiving either control hamster Ig (E–H) or anti-α1 mAb treatment. (I–L). Limbs were photographed (A, E, I), excised, and tissue sections stained either with hematoxylin/eosin (B–C, F–G, J–K) or with toluidine blue to detect proteoglycan (D, H, L). Magnification: ×16 (B, F, J); ×160 (C, G, K); ×200 (D, H, L).

Effect of anti-α1 mAb treatment on the immunopathology of arthritic joints. Joints from wild-type arthritic mice (day 8) receiving either control mAb or anti-α1 mAb treatment were compared visually and histologically to joints from a normal untreated mouse (FIG. 10). Visually, joints from control mAb-treated mice demonstrated redness and swelling of the entire foot including digits, while anti-α1 mAb-treated mice showed little if any signs of inflammation in either joints or digits. Histologic examination showed severe changes in control mAb-treated arthritic joints, with extensive infiltration of the subsynovial tissue with inflammatory cells, adherence of cells to the joint surface, and marked cartilage destruction as evidenced by proteoglycan loss (FIG. 10). Consistent with previous reports (Terato et al. 1992 J. Immunol 148:2103–2108; Terato et al. 1995 Autoimmunity 22:137–147), the majority of the infiltrating cells in this model are neutrophils. Anti-α1 mAb treatment of mice dramatically reduced the amount of inflammatory infiltrate and the degree of cartilage destruction (FIG. 10).

Example 11

Figure 11:
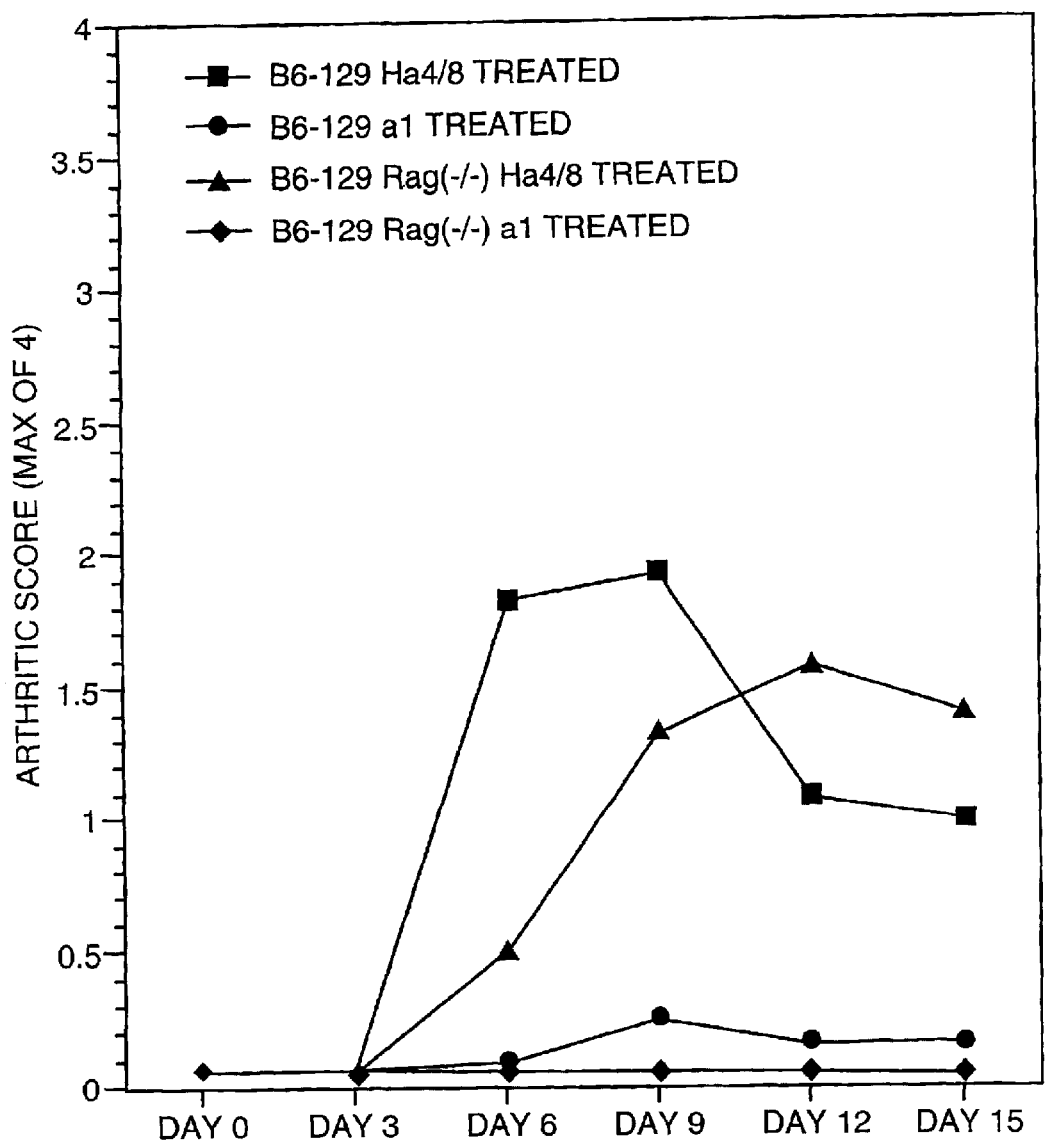
FIG. 11. Development of arthritis is delayed in the absence of lymphocytes and inhibition of arthritis by anti-α1 mAb occurs in the absence of lymphocytes. Wild-type B6,129 or RAG-1-deficient B6,129 mice were treated with anti-collagen mAbs at day 0, followed by LPS on day 3. Arthritis was apparent by day 6 and continued for several weeks. Mice were treated with the indicated mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Development of arthritis is delayed in the absence of lymphocytes and inhibition of arthritis by anti-α1 mAb occurs in the absence of lymphocytes. To determine what cell types might be important in the collagen mAb-induced arthritis model we compared the ability of wild-type B6-129 mice and RAG-1-deficient B6-129 mice to develop arthritis (FIG. 11). Genetic deletion of the RAG-1 (recombination activating gene-1) gene results in a complete loss of mature T and B lymphocytes (Mombaerts et al. 1992 Cell 68:869–877). Both the wild-type and RAG-1-deficient mice developed arthritis, though the kinetics of induction in the RAG-1-deficient mice is significantly slower (FIG. 11). These results suggest that while lymphocytes are involved in this model of arthritis, they are not required for the development and progression of the disease. Published reports examining the effect of the RAG-1-deficient mice in other models of arthritis also found that loss of T and B lymphocytes delayed the onset of arthritis (Plows et al. 1999 J. Immunol. 162:1018–1023). Treatment of either wild-type or RAG-1-deficient mice with anti-α1 mAb completely inhibited arthritis (FIG.11). These results demonstrate that the effectiveness of anti-α1 mAb in this model is not dependent on the presence of lymphocytes, and that as suggested by previous experiments (FIG. 9), the efficacy of anti-α1 mAb in preventing disease may be through its action on other α1-expressing cells, such as macrophages and neutrophils.

Example 12

Figure 12:
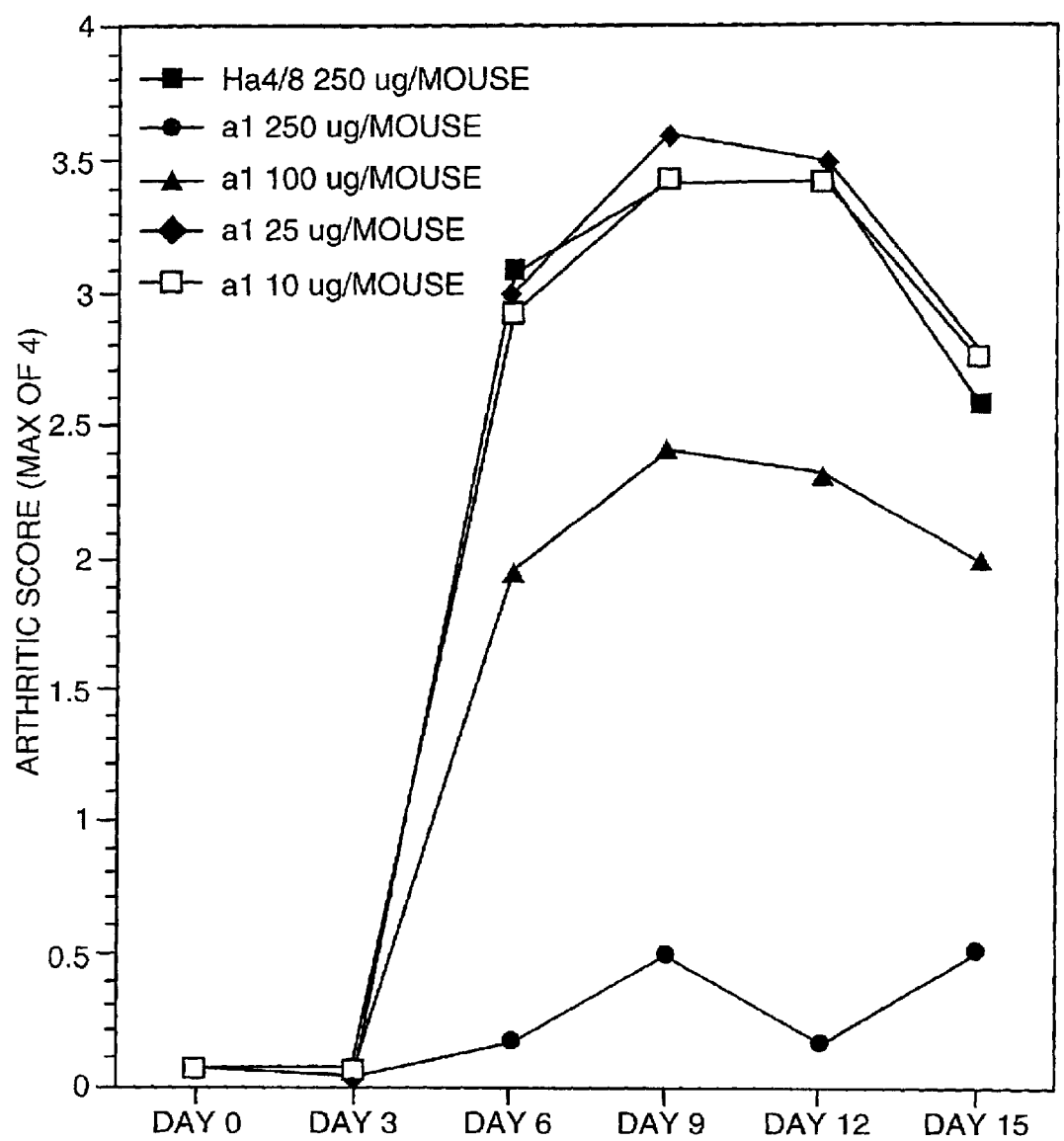
FIG. 12. Dose response of anti-α1 mAb inhibition of arthritis. Wild-type Balb/c mice were treated with anti-collagen mAbs at day 0, followed by LPS on day 3. Arthritis was apparent by day 6 and continued for several weeks. Mice were treated i.p. with the indicated dose of either Ha4/8 (isotype control) or Ha31/8 (anti-α1 mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Dose response of anti-α1 mAb inhibition of arthritis. Given the striking effects of anti-α1 mAb treatment on preventing arthritis, we extended these studies to include a dose response analysis (FIG. 12). Different doses of mAb were administered i.p. every $3^{rd}$ day starting at day 0. In agreement with earlier data, a 250 ug dose of anti-α1 mAb resulted in near complete prevention of arthritis. A lower dose of 100 ug of anti-α1 mAb was partially effective at preventing arthritis in this model, while lower doses did not have any discernable effect on arthritic score (FIG. 12).

Example 13

Figure 13:
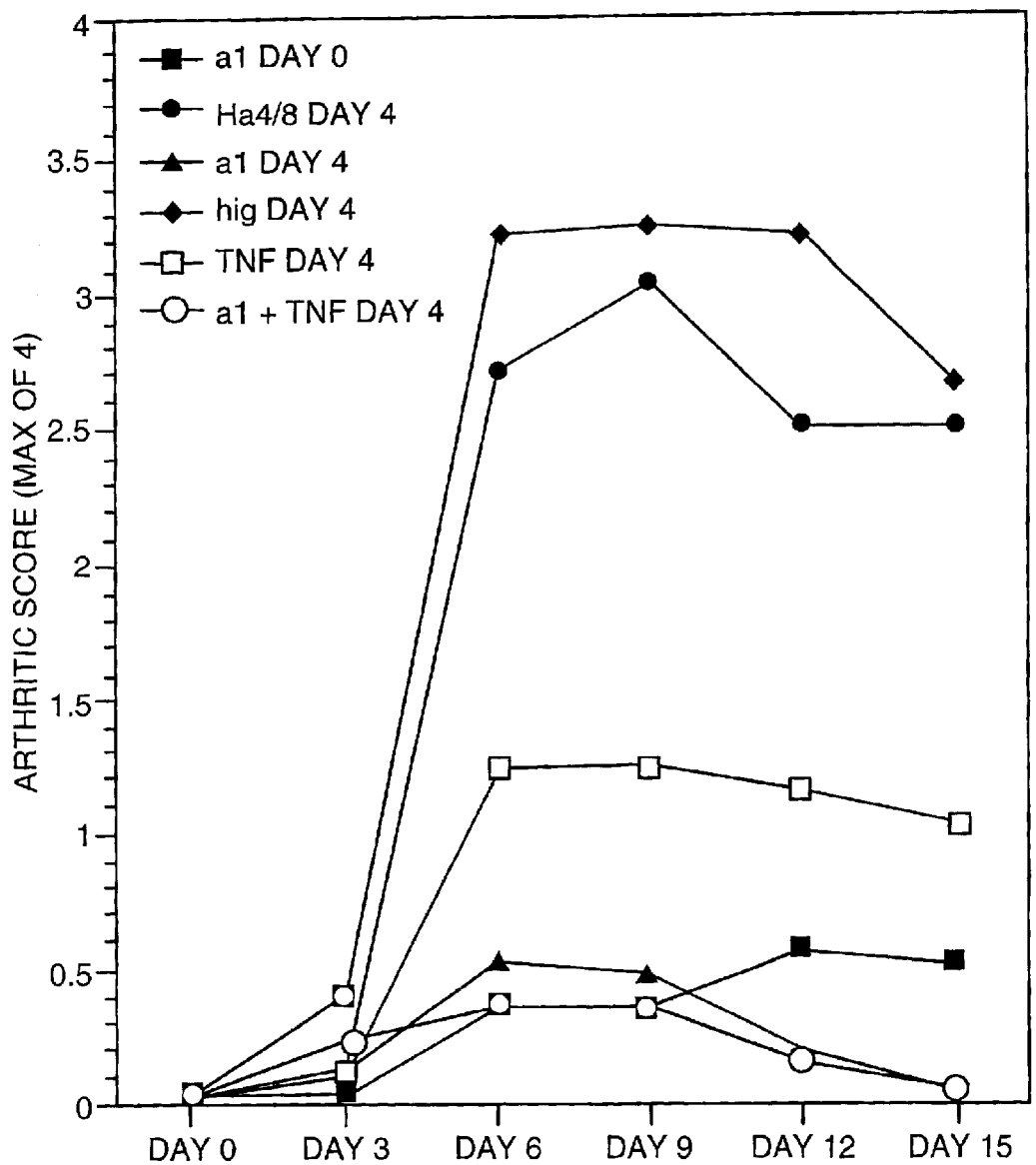
FIG. 13. Therapeutic treatment with anti-α1 mAb can decrease arthritic score. Wild-type Balb/c mice were treated with anti-collagen mAbs at day 0, followed by LPS on day 3. Arthritis was apparent by day 6 and continued for several weeks. Mice were treated i.p. with mAbs (250 ug) or Ig fusion protein (200 ug) every $3^{rd}$ day starting on day 4. Mice received either mAb (Ha4/8 isotype control or Ha31/8 anti-α1), Ig fusion protein (Isotype control Ig or TNF-R55-Ig) or a combination of both (250 ug Ha31/8 and 200 ug TNF-R55-Ig). Each limb was evaluated and scored on a 0 to 4 scale every $3^{rd}$ day. Results are expressed as the mean arthritic score per limb (maximum score of 4). Groups of 4 mice per condition were used.

Therapeutic treatment with anti-α1 mAb can decrease arthritic score. Given the effectiveness of anti-α1 mAb in preventing arthritis, we attempted to treat mice that are on their way to develop disease. Arthritis was induced in mice by injection of a cocktail of anti-collagen type II mAbs on day 0, followed by LPS administration on day 3. Mice were then treated with either anti-α1 mAb or a soluble TNF receptor Ig fusion protein starting on day 4. Progression of arthritis was completely blocked in mice receiving anti-α1 mAb starting at day 4, when compared to mice receiving control hamster mAb starting at day 4 (FIG. 13). The degree of inhibition seen with therapeutic administration of anti-α1 mAb was complete and was equal to that seen with preventative treatment of anti-α1 mAb (started at day 0) (FIG. 13). In comparison, treatment with TNF receptor Ig fusion protein from day 4 onwards resulted in only a 60–70% inhibition in arthritic score when compared to control Ig fusion protein (FIG. 13). Combined treatment of anti-α1 mAb and TNF receptor Ig fusion together was effective at completely inhibiting arthritic score, which is not surprising given the complete effectiveness of anti-α1 mAb treatment alone in suppressing arthritis. In summary, these results indicate that therapeutic treatment with anti-α1 mAb is effective at inhibiting arthritic score, and compares favorably to therapeutic treatment with a TNF antagonist.

Example 14

Cloning and mutagenesis of the α1-I domain. Human and rat α1β1 integrin I domain sequences were amplified from full length cDNAs (Kern, et al. (1994) J. Biol. Chem. 269, 22811–22816; Ignatius et al. (1990) J. Cell Biol. 111, 709–720) by the polymerase chain reaction (PCR) (PCR CORE Kit; Boehringer Mannheim, GmbH Germany), using either human specific (5' CAGGATCCGTCAGCCCCACATTTCAA-3' [forward] (SEQ ID NO: 10); 5' TCCTCGAGGGCTTGCAGGGCAAATAT-3' [reverse] (SEQ ID NO: 11); or rat specific (5'-CAGGATCCGTCAGTCCTACATTTCAA-3' [forward] (SEQ ID NO: 12); 5'-TCCTCGAGCGCTTCCAAAGCGAATAT-3' [reverse] SEQ ID NO: 13) primers. The resulting PCR amplified products were purified, ligated into pGEX4t-i (Pharmacia), and transformed into competent DH5α cells (Life Technologies). Ampicillin resistant colonies were screened for the expression of the ~45 kDa glutathione S-transferase-I domain fusion protein. The sequences from inserts of plasmid DNA of clones that were selected for further characterization were confirmed by DNA sequencing.

A rat/human chimeric α1-I domain (RΔH) was generated (MORPH Mutagenesis kit; 5 prime-3 prime), exchanging the rat residues G91, R92, Q93, and L96 (FIG. 14A) for the corresponding human residues, V, Q, R, and R, respectively. Clones harboring the RΔH I domain were identified by the loss of a diagnostic Stu 1 restriction enzyme site, and the inserts confirmed by DNA sequencing. The amino acid sequence of the human α1-I domain is shown in FIG. 15.

Example 15

Generation of mAbs specific to the –α1 I domain. Monoclonal antibodies have proved to be very useful probes in studying the relationship between structure and function of integrin subunits. For example, mAbs were used extensively to study regions of the β1 subunit associated with an activated conformation (Qu, A., and Leahy, D. J. (1996)

Structure 4, 931–942). Thus, to identify potential probes for conformational changes of the α1-I domain, we generated a panel of mAbs to the human α1-I domain.

Generation of anti-α1 I domain Monoclonal Antibodies. Female Robertsonian mice (Jackson Labs) were immunized intraperitoneally (i.p.) with 25 μg of purified human α1β1 (Edwards et al. (1995) *J. Biol. Chem.* 270, 12635–12640) emulsified with complete Fruend's adjuvant (Life Technologies). They were boosted three times i.p. with 25 μg of α1β1 emulsified with incomplete Fruend's adjuvant (Life Technologies). The mouse with the highest anti-α1-I domain titer was boosted i.p. with 100 μg of α1β1 three days prior to fusion, and intravenously with 50 μg of α1β1 one day prior to fusion. Spleen cells were fused with FL653 myeloma cells at a 1:6 ratio and were plated at 100,000 and 33,000 per well into 96 well tissue culture plates.

Supernatants were assessed for binding to the α1β1 integrin by single color FACS. Prior to FACS analysis, supernatants were incubated with untransfected K562 cells to eliminate IgG that bound solely to the β subunit. Subsequently, 3–5×10$^4$ K562 cells transfected with the α1 integrin subunit (K562-α1) suspended in FACS buffer (1% fetal calf serum (FCS) in PBS containing 0.5% $NaN_3$) were incubated with supernatant for 45 minutes at 4° C., washed and incubated with anti-mouse IgG conjugated to phycoerythrin. After washing twice with FACS buffer, cells were analyzed in a Becton Dickinson Flow Cytometer.

Supernatants from the resulting hybridomas were screened for binding to the α1-I domain. Briefly, 50 μl of 30 μg/ml human α1-I domain-GST fusion in PBS was coated onto wells of a 96-well plate (Nunc) overnight at 4° C. The plates were washed with PBS, blocked with 1% BSA in PBS and the hybridoma supernatant was incubated with the I domain at room temperature for 1 hour. After extensive washing with PBS containing 0.03% Tween 20, alkaline phosphatase linked anti-mouse IgG (Jackson ImmunoResearch) was added for an additional hour. After a final wash, 1 mg/ml p-nitrophenylphosphate (pNPP) in 0.1 M glycine, 1 mM $ZnCl_2$, and 1 MM $MgCl_2$ was added for 30 minutes at room temperature, and the plates were read at O.D. 405.

Selected supernatants were tested for their ability to inhibit K562-α1 dependent adhesion to Collagen IV. K562-α1 cells were labeled with 2 mM 2',7' (bis-2-carboxyethyl-5 and 6) carboxyfluorescein penta acetoxymethylester (BCECF; Molecular Probes) in DMEM containing 0.25% BSA at 37° C. for 30 minutes. Labeled cells were washed with binding buffer (10 mM Hepes, pH 7.4; 0.9% NaCl; and 2% glucose) and resuspended in binding buffer plus 5 MM $MgCl_2$ at a final concentration of 1×10$^6$ cells/ml. 50 μl of supernatant was incubated with an equal volume of 2×10$^5$ K562-(α1 cells in wells of a 96 well plate. The plate was then centrifuged and the supernatants removed. Cells were resuspended in binding buffer and transferred to wells of a collagen-coated plate and incubated for 1 hour at 37° C. Following incubation, the non-adherent cells were removed by washing three times with binding buffer. Attached cells were analyzed on a Cytofluor (Millipore).

Figure 16A:
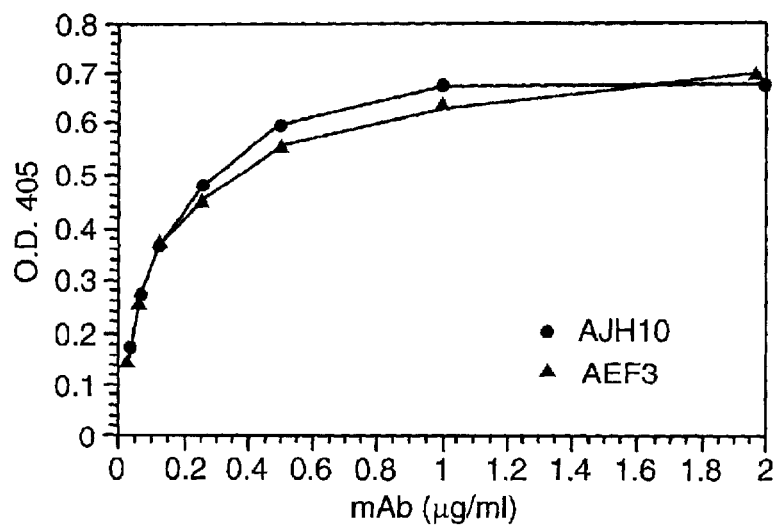
FIG. 16. Identification of a blocking mAb to the α1-I domain. A. Increasing concentration of mAbs AEF3 (triangles) or AJH10 (circles) were bound to plates coated with 30 μg/ml α1-I domain. B. The α1-I domain was treated with increasing concentrations of mAb AJH10 (diamonds) or mAb BGC5 (squares) and bound collagen IV (2 μg/ml) coated plates. C. K562-α1 cell were treated with increasing concentration of mAbs AEF3(triangles) or AJH10 (circles) and bound to collagen IV (5 μg/ml) coated plates. 45–50% of cells added to each well adhered to collagen IV. Data shown is representative of three independent experiments.
Figure 16B:
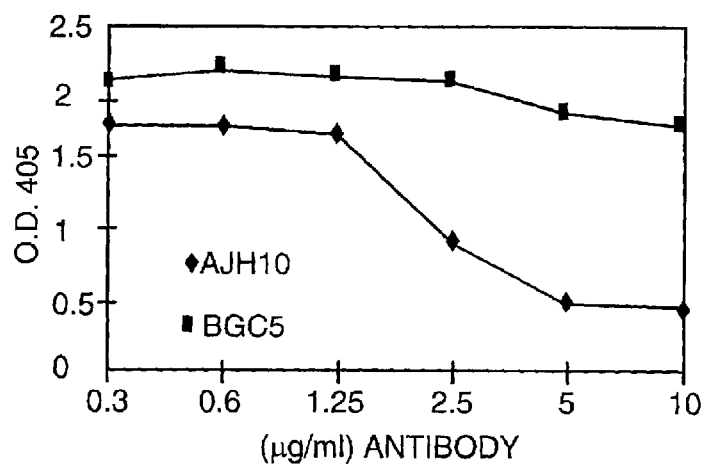
Figure 16C:
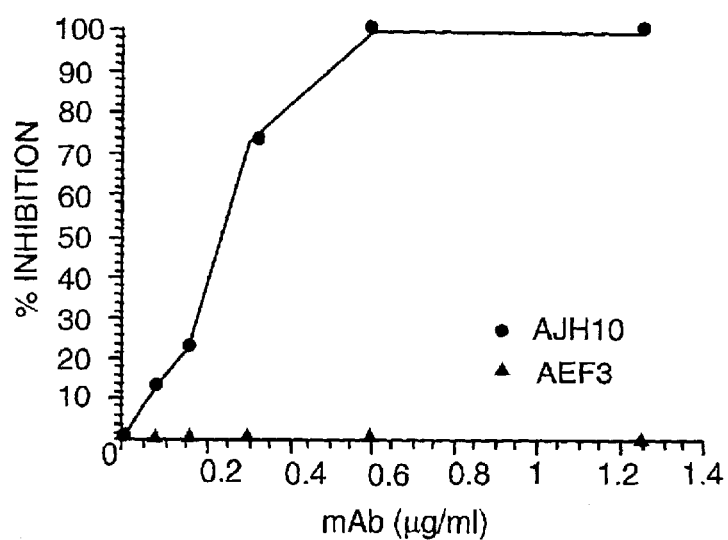

We initially identified 19 hybridomas, the supernatants of which bound to human leukemia K562 cells expressing the α1β1 integrin (K562-α1) and to the α1-I domain. The immunoglobulins were purified from each of these hybridomas and tested for the ability to block either K562-α1 or α1-I domain binding to collagen IV. The mAbs fall into two classes: those that block and those that do not block α1β1 function. For example, while the mAbs produced by clones AEF3, BGC5 and AJH10 bind the α1-I domain (FIG. 16A, data not shown for BGC5), only mAb AJH10 inhibits α1-I domain-dependent (FIG. 16B) or K562-α1 (FIG. 16C) adhesion to collagen IV. The hybridoma that produces the α1 domain antibody AJH10 was deposited under the Budapest Treaty on Aug. 2, 2001 with the American Type Culture Collection, 10801 University Boulevard, Manassas, Va. 20110-2209 (ATCC PTA-3580). Other materials necessary to make AJH10 are available in the public domain to those of ordinary skill in the art.

Sequencing of the Complementarity Determining Regions. To establish the clonal origin of this panel of mAbs, we amplified by PCR and sequenced the CDRs from 12 of the 19 antibodies (data not shown).

2 μg of mRNA, isolated from 10$^7$ hybridomas (FastTrack mRNA isolation kit, Invitrogen), was reverse transcribed (Ready-To-Go You Prime First Strand Kit, Pharmacia Biotech) using 25 pM each of the following primers: heavy chain VH1FOR-2 (Michishita et al. (1993) *Cell* 72, 857–867); light chain, VK4FOR, which defines four separate oligos (Kern et al. (1994) *J. Biol. Chem.* 269, 22811–22816). For each hybridoma, heavy and light chains were amplified in four separate PCR reactions using various combination of the following oligos: 1) Heavy chain: VH1FR1K (Kamata et al. (1995) *J. of Biol. Chem.* 270, 12531–12535), VH1BACK, VH1BACK (Baldwin et al. (1998) *Structure* 6, 923–935), $V_H$fr1a, $V_H$fr1b, $V_H$fr1e, $V_H$fr1f, $V_H$fr1g (Ignatius et al. (1990) *J. Cell Biol.* 111, 709–720), or VH1FOR-2 (Michishita, M., Videm, V., and Arnaout, M. A. (1993) *Cell* 72, 857–867); 2) Light chain: VK1BACK (Baldwin et al. (1998) *Structure* 6, 923–935), VK4FOR, VK2BACK oligos (Kern et al. (1994) *J. Biol. Chem.* 269, 22811–22816), or $V_K$fr1a, $V_H$fr1c, $V_H$fr1e, $V_H$fr1f (Ignatius et al. (1990) *J. Cell Biol.* 111, 709–720). Products were amplified (5 min at 95° C., 50 cycles of 1 min at 94° C., 2 min at 55° C., 2 min at 72° C., and a final cycle of 10 min at 72° C.), gel purified (QIAquick, Qiagen), and sequenced directly using various of the listed oligos on an ABI 377 Sequencer.

Sequences from clones producing function-blocking mAbs were nearly identical across all the complementarity-determining regions (CDRs) and the intervening framework regions suggesting that these hybridomas are clonally related.

Example 16

Immunoblotting and FACS Analysis. Sequences of the variable regions of the non-blocking antibodies were markedly different from the clonally related family of sequences found for the blocking antibodies. As the blocking antibodies appear to originate from a single clone, we chose one (AJH10) to characterize further.

Immunoblotting. The smooth muscle cell layer dissected from sheep aorta, and K562-α1 cells were extracted with 1% Triton X-100 in 50 mM Hepes, pH 7.5, 150 mM NaCl, 10 mM phenylmethylsulfonyl flouride (PMSF), 20 μg/ml aprotinin, 10 μg/ml leupeptin, 10 mM ethylenediaminetetraacetic acid (EDTA). Samples were subjected to 4–20% gradient SDS-PAGE, and electroblotted onto nitrocellulose membranes. The blots were blocked with 5% dry milk in TBS; washed in TBS containing 0.03% Tween-20, and incubated with antibodies in blocking buffer containing 0.05% $NaN_3$ for 2 hours. Blots were then washed as before, incubated with horseradish peroxidase conjugated anti-mouse IgG for one hour, washed again and then treated with ECL reagent (Amersham). Blots were then exposed to film (Kodak) for 30 to 60 seconds, and developed.

Figure 17B:
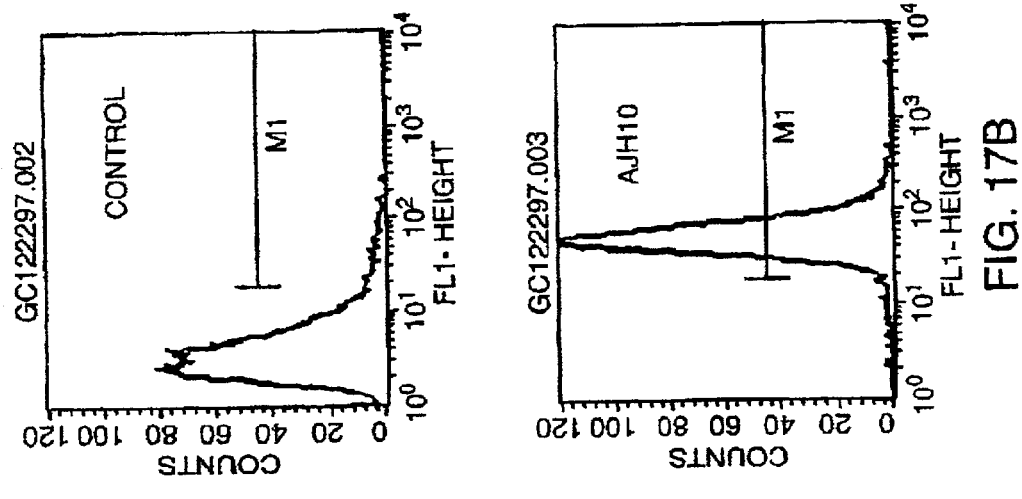
FIG. 17. Species Cross-reactivity of the blocking mAbs. A. Detergents lysates from (1) sheep vascular smooth muscle, (2) human leukemia K562-α1 cells or (3) purified RΔH GST-I domain; (4) Rat GST-α1 I domain; and (5) human GST-α1 I domain were separated by 10–20% SDS-PAGE under non-reducing conditions, and immunoblotted with function-blocking mAb AJH10. Molecular weight markers are shown on the left; non-reduced α1β1 integrin migrates at ~180 kDa; GST-I domain migrates at ~45 kDa. B. Rabbit vascular smooth muscle cells were incubated with either mAb AJH10 (bottom) or murine IgG control (top) and analyzed by fluorescence activated cell sorter (FACS).
Figure 17A:
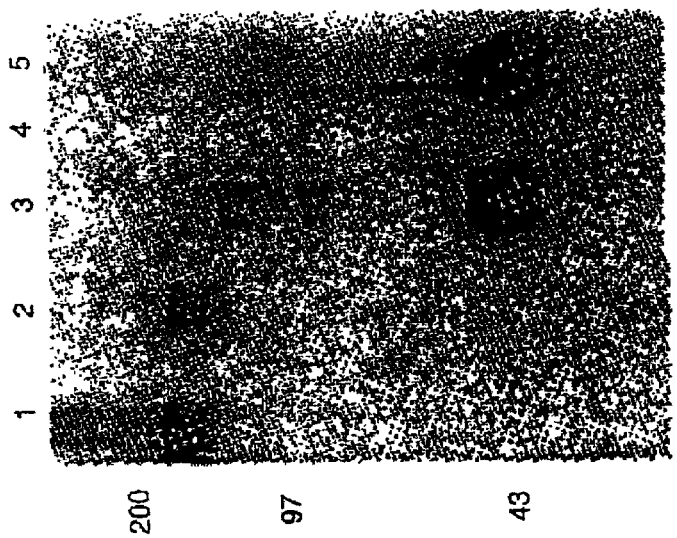

Immunoblotting (FIG. 17A) and FACS analysis (FIG. 17B) demonstrate that AJH10 reacts with human, rabbit, and sheep, but not rat α1β1 integrin suggesting that the blocking mAbs bind to an evolutionarily conserved, linear epitope. The non-blocking mAbs were neither efficient at immunoblotting nor did they react with species other than human.

Example 17

Binding of the α1-I Domain to Collagen is Divalent Cation-dependent

A. Purification of the α1-I Domains.

The α1-I domains were expressed in *E. coli* as GST (glutathione-S-transferase) fusion proteins containing a thrombin cleavage site at the junction of the sequences. The clarified supernatant from cells lysed in PBS was loaded onto a glutathione Sepharose 4B column (Pharmacia) which was washed extensively with PBS. The α1-I domain-GST fusion protein was eluted with 50 mM Tris-HCl, pH 8.0, 5 mM glutathione (reduced). For denaturation studies, the I domain was cleaved with thrombin in 50 mM Tris, pH 7.5, and purified from the GST fusion partner. DTT was added to 2 mM and the sample was loaded on a glutathione Sepharose 4B column. The flow-through and wash fractions were pooled and loaded onto a Q Sepharose FF column (Pharmacia). The α1-I domain was eluted with 50 mM Tris HCl, pH 7.5, 10 mM 2-mercaptoethanol, 75 mM NaCl. The purified I domain displayed its predicted mass (Lee et al. (1995) *Structure* 3, 1333–1340, 871 Da) by electrospray ionization-mass spectrometry (ESI-MS), migrated as a single band by SDS-PAGE, and the protein eluted as a single peak of appropriate size by size exclusion chromatography on a Superose 6 FPLC column (Pharmacia).

B. Functional Analysis 96 well plates were coated overnight at 4° C. with 1 μg/ml collagen IV (Sigma) or collagen Type I (Collaborative Biomedical), washed with Triton buffer (0.1% Triton X-100; 1 mM $MnCl_2$; 25 mM Tris-HCl; 150 mM NaCl), and blocked with 3% bovine serum albumin (BSA) in 25 mM Tris-HCl; 150 mM NaCl (TBS). Serial dilutions of the α1-I domain-GST fusion protein in TBS containing 1 mM $MnCl_2$ and 3% BSA were incubated on the coated plates at room temperature for 1 hour, and washed in Triton buffer. Bound α1-I domain was detected with serial additions of 10 μg/ml biotinylated anti-GST polyclonal antibody (Pharmacia); ExtrAvidin-horseradish peroxidase (Sigma) diluted 1:3000 in TBS containing 1 mM $MnCl_2$ and 3% BSA, and 1-Step ABTS (2,2'-Azine-di[3-ethylbenzthiazoline sulfonate]; Pierce). Plates were read at O.D. 405 on a microplate reader (Molecular Devices).

Results.

Figure 18A:
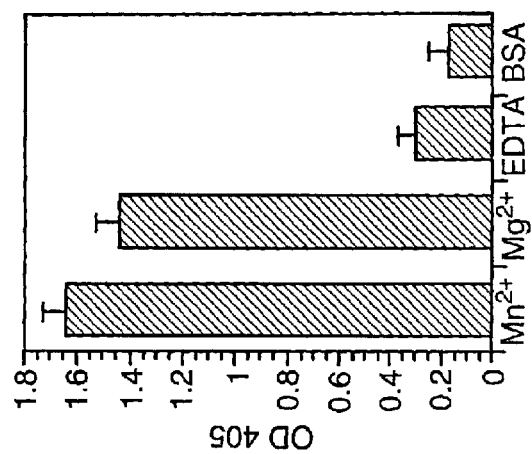
FIG. 18. The α1-I domain binds collagen. A. Increasing concentrations of the human α1-I domain were bound to plates previously coated with 1 μg/ml collagen I (squares) or collagen IV (circles). Values shown have been corrected for background binding to BSA. B. 2 μg/ml human α1-I domain was mixed with increasing concentration of an anti-human α1 integrin antibody 5E8D9 (squares) or an anti-human α2-integrin antibody A2IIE10 (circles), and then bound to plates previously coated with 1 µg/ml collagen IV. C. Plates were coated with 1 µg/ml collagen IV or 3% BSA. α1-I domain (2 µg/ml) was subsequently bound to coated plates in the presence of 1 mM $Mn^{2+}$, 1 mM $Mg^{2+}$, or 5 mM EDTA. Data shown is representative of three independent experiments.
Figure 18B:
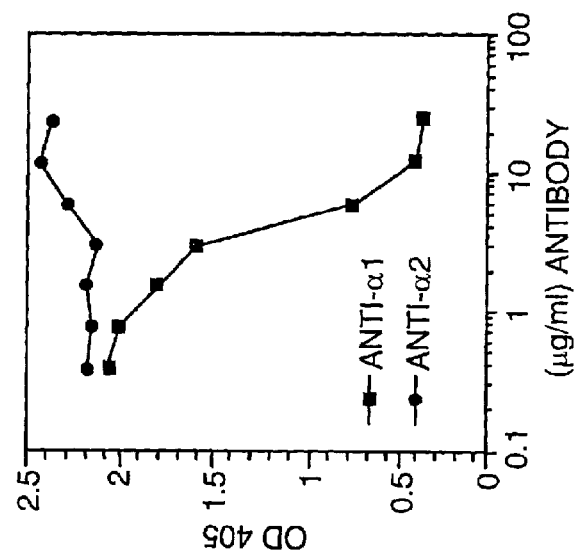
Figure 18C:
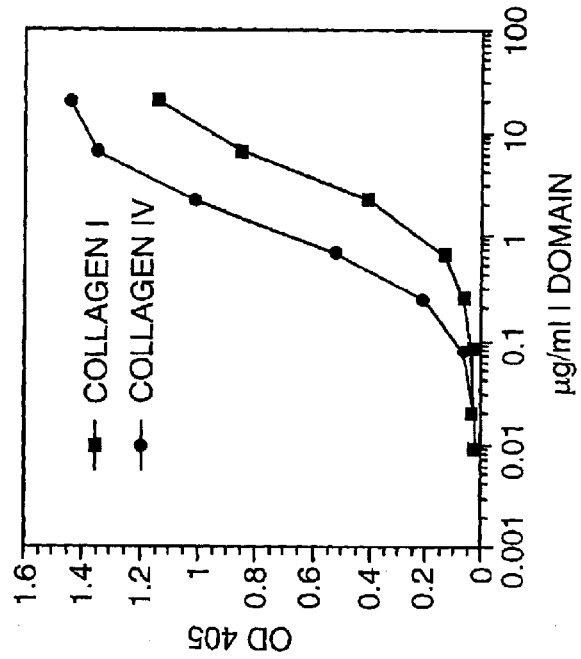

The human and rat (95% identity to human) α1-I domains were expressed in *E. coli* as GST-fusion proteins and purified over glutathione sepharose. Both proteins were examined for binding to collagen I and IV using a variation of an ELISA-based assay previously described (Qu, A., and Leahy, D. J. (1995) *Proc. Natl. Acad. Sci. USA* 92, 10277–10281). The human α1-I domain binds collagen IV with better efficiency than collagen I (FIG. 18A). An antibody specific to the α1-I domain, but not an antibody specific to the α2-I domain (FIG. 18B) abrogated binding to both ligands (data for collagen I is not shown). Both $Mn^{2+}$ and $Mg^{2+}$ stimulated binding, and EDTA reduced binding to background levels (FIG. 18C). No measurable differences in ligand binding were detected between the human and rat α1-I domains suggesting that the sequence differences between species are not functionally relevant (data not shown). Thus, the α1-I domain, specifically, require cation for efficient ligand binding.

Example 18

Figures 14A, 14B:
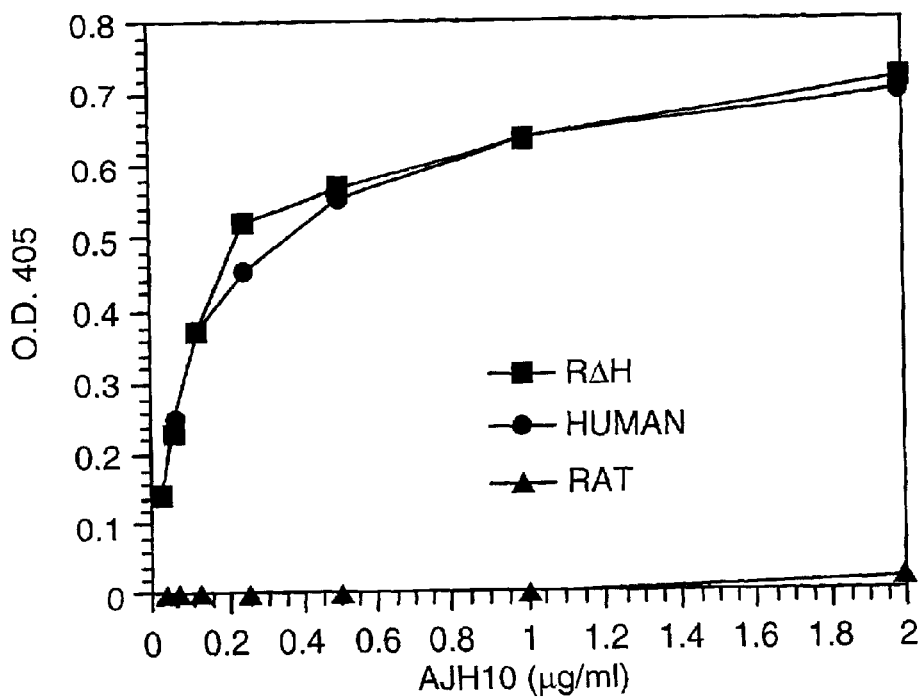
FIG. 14. Location of the Epitope for the anti-α1 domain Blocking mAbs. A. Amino acid sequence of the rat (top) and human (below) α1-I domain. The residues that comprise the MIDAS (metal ion dependent adhesion site) motif are shown in bold. The human amino acids that replaced the corresponding rat residues (RΔH) are shown below the rat sequence in the boxed region. For clarity, residue numbering in the text refers to this figure. B. Increasing concentrations of mAb AJH10 were bound to plates coated with 30 μg/ml human (circles), rat (triangles) or RΔH (squares) α1-I domain. Data shown is representative of three experiments.

A Cation-Dependent Epitope Resides near the MIDAS motif. We exploited the observation that AJH10 recognizes the human, but not the rat α1-I domain sequences to map the epitope for the α1β1 function-blocking mAbs. The human and rat sequences differ by only 12 amino acids, 4 of which lie in a stretch of 6 amino acids (aa 9196, FIG. 14A) adjacent to the critical glutamine (FIG. 14A, aa 97) within the MIDAS motif. To test the hypothesis that the 6 amino acid residues, Val-Gln-Arg-Gly-Gly-Arg, comprise the epitope for the blocking mAbs, we constructed a chimeric I domain (RΔH), exchanging the rat residues G91, R92, Q93, and L96 for the corresponding human residues, V, Q, R, and R, respectively. AJH10, along with all the function-blocking mAbs, recognizes the chimeric I domain (RΔH; FIG. 14B).

To orient these residues with respect to the MIDAS domain in the tertiary structure of the α1-I domain, we modeled the α1-I domain using the coordinates of the crystal structure of the α2 I domain.

A homology model of the human α1 I-domain was built using the X-ray crystal structure of the human α2 I-domain (Ward et al. (1989) *Nature* 341, 544–546). The model was built using the homology modeling module of Insight II (version 2.3.5; Biosym Technologies). The program CHARMM (Clackson et al. (1991) *Nature* 352, 624–628) was used with the all-hydrogen parameter set 22 with a distant dependent dielectric constant of two times the atom separation distance. We first did 1000 steps of steepest descent minimization with mass-weighted harmonic positional constraints of 1 kcal/(mol $Å^2$) on all atoms of the α1-I domain. This minimization was followed by another 1000 steps of steepest descent and 5000 steps of Adopted-Basis Newton Raphson with constraints of 0.1 kcal/(mol $Å^2$) on the C-α atoms of the α1-I domain to avoid significant deviations from the α2-I domain X-ray crystal structure.

The α1β1 and α2β1 integrin sequences exhibit 51% identity with no insertions or deletions, suggesting that the overall structure of the two I domains will be similar. The metal coordination site is predicted to be the same in the α1-I domain as in the α2-I domain, and the residues that comprise the epitope for the blocking mAbs lie on a loop between helix α3 and helix α4 which contains the threonine within the MIDAS motif critical for cation binding. The α1-I domain model predicts that the amide nitrogen of Q92 (FIG. 14A) hydrogen bonds with the carbonyl group of I33, the residue adjacent to S32. Thus, the loop that contains the epitope may play a functional role in stabilizing the MIDAS region.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

What is claimed is:

1. A method for the treatment of arthritis comprising administering to a subject suffering from arthritis a composition comprising a function blocking antibody or a fragment of said antibody, wherein said antibody or fragment of said antibody is capable of binding an epitope of VLA-1, and wherein the epitope consists of the amino acids Val-Gln-Arg-Gly-Gly-Arg (SEQ ID NO:8), to provide a decrease in arthritic score of about 65% or greater when compared to a control antibody treated subject.

2. A method according to claim 1 wherein the decrease in arthritic score is about 79% or greater.

3. A method according to claim 1 wherein the decrease in arthritic score is about 85% or greater.

4. A method according to claim 1 wherein the decrease in arthritic score is about 90% or greater.

5. A method according to claim 1, wherein the antibody is monoclonal.

6. A method according to claim 1, wherein the subject is a human.

7. A method according to claim 1, wherein the subject suffers from rheumatoid arthritis.

* * * * *

SEQUENCE LISTING

<160> NUMBER OF SEQ ID NOS: 13

<210> SEQ ID NO 1
<211> LENGTH: 26
<212> TYPE: DNA
<213> ORGANISM: Homo Sapiens

<400> SEQUENCE: 1
caggatccgt cagccccaca tttcaa                                              26

<210> SEQ ID NO 2
<211> LENGTH: 26
<212> TYPE: DNA
<213> ORGANISM: Homo Sapiens

<400> SEQUENCE: 2
tcctcgaggg cttgcagggc aaatat                                              26

<210> SEQ ID NO 3
<211> LENGTH: 26
<212> TYPE: DNA
<213> ORGANISM: rat

<400> SEQUENCE: 3
caggatccgt cagtcctaca tttcaa                                              26

<210> SEQ ID NO 4
<211> LENGTH: 26
<212> TYPE: DNA
<213> ORGANISM: rat

<400> SEQUENCE: 4
tcctcgagcg cttccaaagc gaatat                                              26

<210> SEQ ID NO 5
<211> LENGTH: 212
<212> TYPE: PRT
<213> ORGANISM: rat

<400> SEQUENCE: 5

Val Ser Pro Thr Phe Gln Val Val Asn Ser Phe Ala Pro Val Gln Glu
 1               5                  10                  15

Cys Ser Thr Gln Leu Asp Ile Val Ile Val Leu Asp Gly Ser Asn Ser
                20                  25                  30

Ile Tyr Pro Trp Glu Ser Val Ile Ala Phe Leu Asn Asp Leu Leu Lys
            35                  40                  45

Arg Met Asp Ile Gly Pro Lys Gln Thr Gln Val Gly Ile Val Gln Tyr
        50                  55                  60

Gly Glu Asn Val Thr His Glu Phe Asn Leu Asn Lys Tyr Ser Ser Thr
    65                  70                  75                  80

Glu Glu Val Leu Val Ala Ala Lys Lys Ile Gly Arg Gln Gly Gly Leu
                85                  90                  95

Gln Thr Met Thr Ala Leu Gly Ile Asp Thr Ala Arg Lys Glu Ala Phe
               100                 105                 110

Thr Glu Arg Ala Arg Arg Gly Val Lys Lys Val Met Val Ile Val Thr
           115                 120                 125

Asp Gly Glu Ser His Asp Asn Tyr Arg Leu Lys Gln Val Ile Gln Asp
       130                 135                 140

```
Cys Glu Asp Glu Asn Ile Gln Arg Phe Ser Ile Ala Ile Leu Gly His
145                 150                 155                 160

Tyr Asn Arg Gly Asn Leu Ser Thr Glu Lys Phe Val Glu Glu Ile Lys
                165                 170                 175

Ser Ile Ala Ser Glu Pro Thr Glu Lys His Phe Phe Asn Val Ser Asp
            180                 185                 190

Glu Leu Ala Leu Val Thr Ile Val Lys Ala Leu Gly Glu Arg Ile Phe
        195                 200                 205

Ala Leu Glu Ala
        210

<210> SEQ ID NO 6
<211> LENGTH: 212
<212> TYPE: PRT
<213> ORGANISM: Homo Sapiens

<400> SEQUENCE: 6

Val Ser Pro Thr Phe Gln Val Val Asn Ser Ile Ala Pro Val Gln Glu
1               5                   10                  15

Cys Ser Thr Gln Leu Asp Ile Val Ile Val Leu Asp Gly Ser Asn Ser
            20                  25                  30

Ile Tyr Pro Trp Asp Ser Val Thr Ala Phe Leu Asn Asp Leu Leu Lys
        35                  40                  45

Arg Met Asp Ile Gly Pro Lys Gln Thr Gln Val Gly Ile Val Gln Tyr
    50                  55                  60

Gly Glu Asn Val Thr His Glu Phe Asn Leu Asn Lys Tyr Ser Ser Thr
65                  70                  75                  80

Glu Glu Val Leu Val Ala Ala Lys Lys Ile Val Gln Arg Gly Gly Arg
                85                  90                  95

Gln Thr Met Thr Ala Leu Gly Thr Asp Thr Ala Arg Lys Glu Ala Phe
            100                 105                 110

Thr Glu Arg Ala Arg Arg Gly Val Lys Lys Val Met Val Ile Val Thr
        115                 120                 125

Asp Gly Glu Ser His Asp Asn His Arg Leu Lys Lys Val Ile Gln Asp
    130                 135                 140

Cys Glu Asp Glu Asn Ile Gln Arg Phe Ser Ile Ala Ile Leu Gly Ser
145                 150                 155                 160

Tyr Asn Arg Gly Asn Leu Ser Thr Glu Lys Phe Val Glu Glu Ile Lys
                165                 170                 175

Ser Ile Ala Ser Glu Pro Thr Glu Lys His Phe Phe Asn Val Ser Asp
            180                 185                 190

Glu Leu Ala Leu Val Thr Ile Val Lys Thr Leu Gly Glu Arg Ile Phe
        195                 200                 205

Ala Leu Glu Ala
        210

<210> SEQ ID NO 7
<211> LENGTH: 6
<212> TYPE: PRT
<213> ORGANISM: rat

<400> SEQUENCE: 7

Gly Arg Gln Gly Gly Leu
1               5

<210> SEQ ID NO 8
<211> LENGTH: 6
```

```
<212> TYPE: PRT
<213> ORGANISM: Homo Sapiens

<400> SEQUENCE: 8

Val Gln Arg Gly Gly Arg
  1               5

<210> SEQ ID NO 9
<211> LENGTH: 6
<212> TYPE: PRT
<213> ORGANISM: Homo Sapiens

<400> SEQUENCE: 9

Val Gln Arg Gly Gly Arg
  1               5

<210> SEQ ID NO 10
<211> LENGTH: 26
<212> TYPE: DNA
<213> ORGANISM: Homo Sapiens

<400> SEQUENCE: 10
caggatccgt cagccccaca tttcaa                                              26

<210> SEQ ID NO 11
<211> LENGTH: 26
<212> TYPE: DNA
<213> ORGANISM: Homo Sapiens

<400> SEQUENCE: 11
tcctcgaggg cttgcagggc aaatat                                              26

<210> SEQ ID NO 12
<211> LENGTH: 26
<212> TYPE: DNA
<213> ORGANISM: rat

<400> SEQUENCE: 12
caggatccgt cagtcctaca tttcaa                                              26

<210> SEQ ID NO 13
<211> LENGTH: 26
<212> TYPE: DNA
<213> ORGANISM: rat

<400> SEQUENCE: 13
tcctcgagcg cttccaaagc gaatat                                              26
```